(12) United States Patent
Elimelech et al.

(10) Patent No.: US 12,417,595 B2
(45) Date of Patent: Sep. 16, 2025

(54) AUGMENTED-REALITY SURGICAL SYSTEM USING DEPTH SENSING

(71) Applicant: AUGMEDICS LTD., Yokneam Illit (IL)

(72) Inventors: Nissan Elimelech, Beerotaim (IL); Stuart Wolf, Yokneam (IL); Nitzan Krasney, Haifa (IL); Monica Marie Kuhnert, Chicago, IL (US)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

(21) Appl. No.: 18/365,844

(22) Filed: Aug. 4, 2023

(65) Prior Publication Data

US 2023/0410445 A1  Dec. 21, 2023

Related U.S. Application Data

(63) Continuation of application No. PCT/IB2022/057733, filed on Aug. 18, 2022.
(Continued)

(51) Int. Cl.
*G06T 19/00* (2011.01)
*A61B 34/20* (2016.01)
(Continued)

(52) U.S. Cl.
CPC ............ *G06T 19/006* (2013.01); *A61B 34/20* (2016.02); *A61B 90/37* (2016.02);
(Continued)

(58) Field of Classification Search
None
See application file for complete search history.

(56) References Cited

U.S. PATENT DOCUMENTS

| 3,101,715 A | 8/1963 | Glassman |
| 3,690,776 A | 9/1972 | Zaporoshan |

(Continued)

FOREIGN PATENT DOCUMENTS

| CA | 3022448 A1 | 2/2018 |
| CA | 3034314 A1 | 2/2018 |

(Continued)

OTHER PUBLICATIONS

Lee, Sing Chun, et al. "Multi-modal imaging, model-based tracking, and mixed reality visualisation for orthopaedic surgery." Healthcare technology letters 4.5 (2017): 168-173.*

(Continued)

*Primary Examiner* — Ryan M Gray
(74) *Attorney, Agent, or Firm* — Dinsmore & Shohl LLP

(57) ABSTRACT

Disclosed herein are systems, devices, and methods for image-guided surgery. Some systems include a head-mounted unit, having a see-through augmented-reality display and a depth sensor, which is configured to generate depth data with respect to a region of interest (ROI) of a body of a patient that is viewed through the display by a user wearing the head-mounted unit. A processor, which is configured to receive a three-dimensional (3D) tomographic image of the body of the patient, computes a depth map of the ROI based on the depth data generated by the depth sensor, to compute a transformation over the ROI so as to register the tomographic image with the depth map, and to apply the transformation in presenting a part of the tomographic image on the display in registration with the ROI viewed through the display.

20 Claims, 9 Drawing Sheets

Related U.S. Application Data

(60) Provisional application No. 63/281,677, filed on Nov. 21, 2021, provisional application No. 63/236,241, filed on Aug. 24, 2021, provisional application No. 63/236,244, filed on Aug. 24, 2021, provisional application No. 63/234,272, filed on Aug. 18, 2021.

(51) Int. Cl.
*A61B 90/00* (2016.01)
*G02B 27/01* (2006.01)
*G06T 7/00* (2017.01)
*G06T 7/30* (2017.01)
*G06T 7/521* (2017.01)
*G06T 7/55* (2017.01)
*G06T 7/593* (2017.01)
*G06T 7/62* (2017.01)
*G06T 7/73* (2017.01)
*H04N 13/128* (2018.01)
*H04N 13/156* (2018.01)
*H04N 13/167* (2018.01)
*H04N 13/239* (2018.01)
*H04N 13/344* (2018.01)
*H04N 13/383* (2018.01)
*H04N 23/11* (2023.01)
*A61B 34/10* (2016.01)

(52) U.S. Cl.
CPC ........ *G02B 27/0172* (2013.01); *G06T 7/0016* (2013.01); *G06T 7/30* (2017.01); *G06T 7/521* (2017.01); *G06T 7/55* (2017.01); *G06T 7/593* (2017.01); *G06T 7/62* (2017.01); *G06T 7/73* (2017.01); *H04N 13/128* (2018.05); *H04N 13/156* (2018.05); *H04N 13/167* (2018.05); *H04N 13/239* (2018.05); *H04N 13/344* (2018.05); *H04N 13/383* (2018.05); *H04N 23/11* (2023.01); *A61B 2034/107* (2016.02); *A61B 2090/365* (2016.02); *A61B 2090/367* (2016.02); *A61B 2090/371* (2016.02); *A61B 2090/373* (2016.02); *G02B 2027/0134* (2013.01); *G02B 2027/0138* (2013.01); *G02B 2027/014* (2013.01); *G02B 2027/0141* (2013.01); *G02B 2027/0178* (2013.01); *G06T 2200/04* (2013.01); *G06T 2207/10012* (2013.01); *G06T 2207/10028* (2013.01); *G06T 2207/10081* (2013.01); *G06T 2207/20084* (2013.01); *G06T 2207/30008* (2013.01); *G06T 2207/30012* (2013.01); *G06T 2207/30204* (2013.01); *G06T 2210/12* (2013.01); *G06T 2210/41* (2013.01)

(56) References Cited

U.S. PATENT DOCUMENTS

| | | |
|---|---|---|
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,100,420 A | 3/1992 | Green et al. |
| 5,147,365 A | 9/1992 | Whitlock et al. |
| 5,357,292 A | 10/1994 | Wiedner |
| 5,410,802 A | 5/1995 | Buckley |
| 5,441,042 A | 8/1995 | Putman |
| 5,442,146 A | 8/1995 | Bell et al. |
| 5,510,832 A | 4/1996 | Garcia |
| D370,309 S | 5/1996 | Stucky |
| 5,620,188 A | 4/1997 | McCurry et al. |
| 5,636,255 A | 6/1997 | Ellis |
| 5,665,092 A | 9/1997 | Mangiardi et al. |
| 5,743,731 A | 4/1998 | Lares et al. |
| 5,771,121 A | 6/1998 | Hentschke |
| 5,792,046 A | 8/1998 | Dobrovolny |
| 5,841,507 A | 11/1998 | Barnes |
| 6,006,126 A | 12/1999 | Cosman |
| 6,038,467 A | 3/2000 | De Bliek et al. |
| 6,125,164 A | 9/2000 | Murphy et al. |
| 6,138,530 A | 10/2000 | McClure |
| 6,147,805 A | 11/2000 | Fergason |
| 6,227,667 B1 | 5/2001 | Halldorsson et al. |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,447,503 B1 | 9/2002 | Wynne et al. |
| 6,449,090 B1 | 9/2002 | Omar et al. |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa et al. |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto et al. |
| 6,740,882 B2 | 5/2004 | Weinberg |
| 6,757,068 B2 | 6/2004 | Foxlin |
| 6,759,200 B1 | 7/2004 | Stanton, Jr. |
| 6,847,336 B1 | 1/2005 | Lemelson et al. |
| 6,856,324 B2 | 2/2005 | Sauer et al. |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini et al. |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers et al. |
| 7,141,812 B2 | 11/2006 | Appleby et al. |
| 7,157,459 B2 | 1/2007 | Ohta et al. |
| 7,169,785 B2 | 1/2007 | Timmer et al. |
| 7,171,255 B2 | 1/2007 | Holupka et al. |
| 7,176,936 B2 | 2/2007 | Sauer et al. |
| 7,187,792 B2 | 3/2007 | Fu et al. |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Lechot |
| 7,231,076 B2 | 6/2007 | Fu et al. |
| 7,235,076 B2 | 6/2007 | Pacheco |
| 7,239,330 B2 | 7/2007 | Sauer et al. |
| 7,241,292 B2 | 7/2007 | Hooven |
| 7,259,266 B2 | 8/2007 | Carter et al. |
| 7,260,426 B2 | 8/2007 | Schweikard et al. |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang et al. |
| 7,359,535 B2 | 4/2008 | Salla et al. |
| 7,364,314 B2 | 4/2008 | Nilsen et al. |

(56) References Cited

U.S. PATENT DOCUMENTS

| | | |
|---|---|---|
| 7,366,934 B1 | 4/2008 | Narayan et al. |
| 7,379,077 B2 | 5/2008 | Bani-Hashemi et al. |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley et al. |
| 7,462,852 B2 | 12/2008 | Appleby et al. |
| 7,493,153 B2 | 2/2009 | Ahmed et al. |
| 7,505,617 B2 | 3/2009 | Fu et al. |
| 7,507,968 B2 | 3/2009 | Wollenweber et al. |
| 7,518,136 B2 | 4/2009 | Appleby et al. |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton et al. |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson et al. |
| 7,620,223 B2 | 11/2009 | Xu et al. |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood et al. |
| 7,645,050 B2 | 1/2010 | Wilt et al. |
| 7,653,226 B2 | 1/2010 | Guhring et al. |
| 7,657,075 B2 | 2/2010 | Viswanathan |
| 7,689,019 B2 | 3/2010 | Boese et al. |
| 7,689,042 B2 | 3/2010 | Brunner et al. |
| 7,689,320 B2 | 3/2010 | Prisco et al. |
| 7,699,486 B1 | 4/2010 | Beiner |
| 7,699,793 B2 | 4/2010 | Goette et al. |
| 7,719,769 B2 | 5/2010 | Sugihara et al. |
| D617,825 S | 6/2010 | Chang |
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein et al. |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson, Jr. |
| 7,835,778 B2 | 11/2010 | Foley et al. |
| 7,835,784 B2 | 11/2010 | Mire et al. |
| 7,837,987 B2 | 11/2010 | Shi et al. |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon et al. |
| 7,854,705 B2 | 12/2010 | Pawluczyk et al. |
| 7,857,271 B2 | 12/2010 | Lees |
| 7,860,282 B2 | 12/2010 | Boese et al. |
| D630,766 S | 1/2011 | Harbin |
| 7,865,269 B2 | 1/2011 | Prisco et al. |
| 7,874,686 B2 | 1/2011 | Rossner et al. |
| 7,881,770 B2 | 2/2011 | Melkent et al. |
| 7,893,413 B1 | 2/2011 | Appleby et al. |
| 7,894,649 B2 | 2/2011 | Fu et al. |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani et al. |
| 7,953,471 B2 | 5/2011 | Clayton et al. |
| 7,969,383 B2 | 6/2011 | Eberl et al. |
| 7,974,677 B2 | 7/2011 | Mire et al. |
| 7,985,756 B2 | 7/2011 | Barlow et al. |
| 7,991,557 B2 | 8/2011 | Liew et al. |
| 7,993,353 B2 | 8/2011 | Roner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong et al. |
| 8,045,266 B2 | 10/2011 | Nakamura |
| 8,060,181 B2 | 11/2011 | Rodriguez et al. |
| 8,068,581 B2 | 11/2011 | Boese et al. |
| 8,068,896 B2 | 11/2011 | Daghighian et al. |
| 8,077,943 B2 | 12/2011 | Williams et al. |
| 8,079,957 B2 | 12/2011 | Ma et al. |
| 8,081,812 B2 | 12/2011 | Kreiser |
| 8,085,075 B2 | 12/2011 | Huffman et al. |
| 8,085,897 B2 | 12/2011 | Morton |
| 8,090,175 B2 | 1/2012 | Fu et al. |
| 8,092,400 B2 | 1/2012 | Warkentine et al. |
| 8,108,072 B2 | 1/2012 | Zhao et al. |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman et al. |
| 8,180,132 B2 | 5/2012 | Gorges et al. |
| 8,180,429 B2 | 5/2012 | Sasso |
| 8,208,599 B2 | 6/2012 | Ye et al. |
| 8,216,211 B2 | 7/2012 | Mathis et al. |
| 8,221,402 B2 | 7/2012 | Francischelli et al. |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese et al. |
| 8,300,315 B2 | 10/2012 | Kobayashi |
| 8,305,685 B2 | 11/2012 | Heine et al. |
| 8,306,305 B2 | 11/2012 | Porat et al. |
| 8,309,932 B2 | 11/2012 | Haselman et al. |
| 8,317,320 B2 | 11/2012 | Huang |
| 8,328,815 B2 | 12/2012 | Farr et al. |
| 8,335,553 B2 | 12/2012 | Rubner et al. |
| 8,335,557 B2 | 12/2012 | Maschke |
| 8,340,379 B2 | 12/2012 | Razzaque et al. |
| 8,369,925 B2 | 2/2013 | Giesel et al. |
| 8,386,022 B2 | 2/2013 | Jutras et al. |
| 8,394,144 B2 | 3/2013 | Zehavi et al. |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick et al. |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson et al. |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar et al. |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon et al. |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park et al. |
| 8,686,923 B2 | 4/2014 | Eberl et al. |

(56) References Cited

U.S. PATENT DOCUMENTS

| | | | |
|---|---|---|---|
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann et al. |
| 8,699,765 B2 | 4/2014 | Hao et al. |
| 8,705,829 B2 | 4/2014 | Frank et al. |
| 8,737,708 B2 | 5/2014 | Hartmann et al. |
| 8,746,887 B2 | 6/2014 | Shestak et al. |
| 8,764,025 B1 | 7/2014 | Gao |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu et al. |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin et al. |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo et al. |
| 8,890,773 B1 | 11/2014 | Pederson |
| 8,890,943 B2 | 11/2014 | Lee et al. |
| 8,897,514 B2 | 11/2014 | Feikas et al. |
| 8,900,131 B2 | 12/2014 | Chopra et al. |
| 8,903,150 B2 | 12/2014 | Star-Lack et al. |
| 8,908,952 B2 | 12/2014 | Isaacs et al. |
| 8,911,358 B2 | 12/2014 | Koninckx et al. |
| 8,917,268 B2 | 12/2014 | Johnsen et al. |
| 8,920,776 B2 | 12/2014 | Gaiger et al. |
| 8,922,589 B2 | 12/2014 | Laor |
| 8,941,559 B2 | 1/2015 | Bar-Zeev et al. |
| 8,942,455 B2 | 1/2015 | Chou et al. |
| 8,950,877 B2 | 2/2015 | Northey et al. |
| 8,953,246 B2 | 2/2015 | Koenig |
| 8,961,500 B2 | 2/2015 | Dicorleto et al. |
| 8,965,583 B2 | 2/2015 | Ortmaier et al. |
| 8,969,829 B2 | 3/2015 | Wollenweber et al. |
| 8,989,349 B2 | 3/2015 | Thomson et al. |
| 8,992,580 B2 | 3/2015 | Bar et al. |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck et al. |
| 9,060,757 B2 | 6/2015 | Lawson et al. |
| 9,066,751 B2 | 6/2015 | Sasso |
| 9,081,436 B1 | 7/2015 | Berme et al. |
| 9,084,635 B2 | 7/2015 | Nuckley et al. |
| 9,085,643 B2 | 7/2015 | Svanborg et al. |
| 9,087,471 B2 | 7/2015 | Miao |
| 9,100,643 B2 | 8/2015 | McDowall et al. |
| 9,101,394 B2 | 8/2015 | Arata et al. |
| 9,104,902 B2 | 8/2015 | Xu et al. |
| 9,111,175 B2 | 8/2015 | Strommer et al. |
| 9,123,155 B2 | 9/2015 | Cunningham et al. |
| 9,125,556 B2 | 9/2015 | Zehavi et al. |
| 9,129,054 B2 | 9/2015 | Nawana et al. |
| 9,129,372 B2 | 9/2015 | Kriston et al. |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby et al. |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella et al. |
| 9,240,046 B2 | 1/2016 | Carrell et al. |
| 9,244,278 B2 | 1/2016 | Sugiyama et al. |
| 9,247,240 B2 | 1/2016 | Park et al. |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Rodriguez Ponce |
| 9,286,730 B2 | 3/2016 | Bar-Zeev et al. |
| 9,289,267 B2 | 3/2016 | Sauer et al. |
| 9,294,222 B2 | 3/2016 | Proctor, Jr. |
| 9,300,949 B2 | 3/2016 | Ahearn |
| 9,305,354 B2 | 4/2016 | Burlon et al. |
| 9,310,591 B2 | 4/2016 | Hua et al. |
| 9,320,474 B2 | 4/2016 | Demri et al. |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard et al. |
| 9,344,686 B2 | 5/2016 | Moharir |
| 9,349,066 B2 | 5/2016 | Koo et al. |
| 9,349,520 B2 | 5/2016 | Demetriou et al. |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico et al. |
| 9,387,008 B2 | 7/2016 | Sarvestani et al. |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko et al. |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park et al. |
| 9,443,488 B2 | 9/2016 | Borenstein et al. |
| 9,453,804 B2 | 9/2016 | Tahtali |
| 9,456,878 B2 | 10/2016 | MacFarlane et al. |
| 9,465,235 B2 | 10/2016 | Chang |
| 9,468,373 B2 | 10/2016 | Larsen |
| 9,470,908 B1 | 10/2016 | Frankel et al. |
| 9,473,766 B2 | 10/2016 | Douglas et al. |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Nanqing |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme et al. |
| 9,530,382 B2 | 12/2016 | Simmons |
| 9,532,846 B2 | 1/2017 | Nakamura |
| 9,532,849 B2 | 1/2017 | Anderson et al. |
| 9,533,407 B1 | 1/2017 | Ragner |
| 9,538,962 B1 | 1/2017 | Hannaford et al. |
| 9,545,233 B2 | 1/2017 | Sirpad et al. |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen et al. |
| 9,561,446 B2 | 2/2017 | Brecher |
| 9,565,415 B2 | 2/2017 | Zhang et al. |
| 9,572,661 B2 | 2/2017 | Robin et al. |
| 9,576,398 B2 | 2/2017 | Zehner et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,626,936 B2 | 4/2017 | Bell |
| 9,629,595 B2 | 4/2017 | Walker et al. |
| 9,633,431 B2 | 4/2017 | Merlet |

(56) References Cited

U.S. PATENT DOCUMENTS

| | | |
|---|---|---|
| 9,645,395 B2 | 5/2017 | Bolas et al. |
| 9,646,423 B1 | 5/2017 | Sun et al. |
| 9,672,597 B2 | 6/2017 | Amiot et al. |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque et al. |
| 9,684,980 B2 | 6/2017 | Royalty et al. |
| 9,690,119 B2 | 6/2017 | Garofolo et al. |
| RE46,463 E | 7/2017 | Fienbloom et al. |
| 9,693,748 B2 | 7/2017 | Rai et al. |
| 9,710,968 B2 | 7/2017 | Dillavou et al. |
| 9,713,502 B2 | 7/2017 | Finkman et al. |
| 9,724,119 B2 | 8/2017 | Hissong et al. |
| 9,724,165 B2 | 8/2017 | Arata et al. |
| 9,726,888 B2 | 8/2017 | Giartosio et al. |
| 9,728,006 B2 | 8/2017 | Varga |
| 9,729,831 B2 | 8/2017 | Birnkrant et al. |
| 9,746,739 B2 | 8/2017 | Alton et al. |
| 9,757,034 B2 | 9/2017 | Desjardins et al. |
| 9,757,087 B2 | 9/2017 | Simon et al. |
| 9,766,441 B2 | 9/2017 | Rappel |
| 9,766,459 B2 | 9/2017 | Alton et al. |
| 9,767,608 B2 | 9/2017 | Lee et al. |
| 9,770,203 B1 | 9/2017 | Berme et al. |
| 9,772,102 B1 | 9/2017 | Ferguson |
| 9,772,495 B2 | 9/2017 | Tam et al. |
| 9,791,138 B1 | 10/2017 | Feinbloom et al. |
| 9,800,995 B2 | 10/2017 | Libin et al. |
| 9,805,504 B2 | 10/2017 | Zhang et al. |
| 9,808,148 B2 | 11/2017 | Miller et al. |
| 9,839,448 B2 | 12/2017 | Reckling et al. |
| 9,844,413 B2 | 12/2017 | Daon et al. |
| 9,851,080 B2 | 12/2017 | Wilt et al. |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 * | 2/2018 | Cvetko .................. G06T 15/04 |
| 9,898,866 B2 | 2/2018 | Fuchs et al. |
| 9,901,414 B2 | 2/2018 | Lively et al. |
| 9,911,187 B2 | 3/2018 | Steinle et al. |
| 9,911,236 B2 | 3/2018 | Bar et al. |
| 9,927,611 B2 | 3/2018 | Rudy et al. |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards et al. |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Ben-Yishai et al. |
| 10,022,104 B2 | 7/2018 | Sell et al. |
| 10,023,615 B2 | 7/2018 | Bonny |
| 10,026,015 B2 | 7/2018 | Cavusoglu et al. |
| 10,034,713 B2 | 7/2018 | Yang et al. |
| 10,042,167 B2 | 8/2018 | McDowall et al. |
| 10,046,165 B2 | 8/2018 | Frewin et al. |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chung |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom et al. |
| 10,134,166 B2 | 11/2018 | Benishti et al. |
| 10,134,194 B2 | 11/2018 | Kepner et al. |
| 10,139,652 B2 | 11/2018 | Windham |
| 10,139,920 B2 | 11/2018 | Isaacs et al. |
| 10,142,496 B1 | 11/2018 | Rao et al. |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi et al. |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,207,315 B2 | 2/2019 | Appleby et al. |
| 10,212,517 B1 | 2/2019 | Beltran et al. |
| 10,230,719 B2 | 3/2019 | Vaughn et al. |
| 10,231,893 B2 | 3/2019 | Lei et al. |
| 10,235,606 B2 | 3/2019 | Miao et al. |
| 10,240,769 B1 | 3/2019 | Braganca et al. |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca et al. |
| 10,357,146 B2 | 7/2019 | Fiebel et al. |
| 10,357,574 B2 | 7/2019 | Hilderbrand et al. |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Abou Shousha |
| 10,388,076 B2 | 8/2019 | Bar-Zeev et al. |
| 10,398,514 B2 | 9/2019 | Ryan et al. |
| 10,401,657 B2 | 9/2019 | Jiang et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers et al. |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat et al. |
| 10,433,814 B2 | 10/2019 | Razzaque et al. |
| 10,434,335 B2 | 10/2019 | Takahashi et al. |
| 10,441,236 B2 | 10/2019 | Bar-Tal et al. |
| 10,444,514 B2 | 10/2019 | Abou Shousha et al. |

(56) References Cited

U.S. PATENT DOCUMENTS

| | | |
|---|---|---|
| 10,447,947 B2 | 10/2019 | Liu |
| 10,448,003 B2 | 10/2019 | Grafenberg |
| 10,449,040 B2 | 10/2019 | Lashinski et al. |
| 10,453,187 B2 | 10/2019 | Peterson et al. |
| 10,463,434 B2 | 11/2019 | Siegler et al. |
| 10,465,892 B1 | 11/2019 | Feinbloom et al. |
| 10,466,487 B2 | 11/2019 | Blum et al. |
| 10,470,732 B2 | 11/2019 | Baumgart et al. |
| 10,473,314 B1 | 11/2019 | Braganca et al. |
| 10,485,989 B2 | 11/2019 | Jordan et al. |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | Dimaio et al. |
| 10,511,822 B2 | 12/2019 | Casas |
| 10,517,544 B2 | 12/2019 | Taguchi et al. |
| 10,537,395 B2 | 1/2020 | Perez |
| 10,540,780 B1 | 1/2020 | Cousins et al. |
| 10,543,485 B2 | 1/2020 | Ismagilov et al. |
| 10,546,423 B2 | 1/2020 | Jones et al. |
| 10,548,557 B2 | 2/2020 | Lim et al. |
| 10,555,775 B2 | 2/2020 | Hoffman et al. |
| 10,568,535 B2 | 2/2020 | Roberts et al. |
| 10,571,696 B2 | 2/2020 | Urey et al. |
| 10,571,716 B2 | 2/2020 | Chapiro |
| 10,573,086 B2 | 2/2020 | Bar-Zeev et al. |
| 10,573,087 B2 | 2/2020 | Gallop et al. |
| 10,577,630 B2 | 3/2020 | Zhang et al. |
| 10,586,400 B2 | 3/2020 | Douglas |
| 10,591,737 B2 | 3/2020 | Yildiz et al. |
| 10,592,748 B1 | 3/2020 | Cousins et al. |
| 10,594,998 B1 | 3/2020 | Casas |
| 10,595,716 B2 | 3/2020 | Nazareth et al. |
| 10,601,950 B2 | 3/2020 | Devam et al. |
| 10,602,114 B2 | 3/2020 | Casas |
| 10,603,113 B2 | 3/2020 | Lang |
| 10,603,133 B2 | 3/2020 | Wang et al. |
| 10,606,085 B2 | 3/2020 | Toyama |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi et al. |
| 10,626,473 B2 | 4/2020 | Mariani et al. |
| 10,631,905 B2 | 4/2020 | Asfora et al. |
| 10,631,907 B2 | 4/2020 | Zucker et al. |
| 10,634,331 B1 | 4/2020 | Feinbloom et al. |
| 10,634,921 B2 | 4/2020 | Blum et al. |
| 10,638,080 B2 | 4/2020 | Ovchinnikov et al. |
| 10,646,285 B2 | 5/2020 | Siemionow et al. |
| 10,650,513 B2 | 5/2020 | Penney et al. |
| 10,650,594 B2 | 5/2020 | Jones et al. |
| 10,652,525 B2 | 5/2020 | Woods |
| 10,653,495 B2 * | 5/2020 | Gregerson ............. A61B 6/461 |
| 10,660,715 B2 | 5/2020 | Dozeman |
| 10,663,738 B2 | 5/2020 | Carlvik et al. |
| 10,665,033 B2 | 5/2020 | Bar-Zeev et al. |
| 10,670,937 B2 | 6/2020 | Alton et al. |
| 10,672,145 B2 | 6/2020 | Albiol et al. |
| 10,682,112 B2 | 6/2020 | Pizaine et al. |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori et al. |
| 10,706,540 B2 | 7/2020 | Merlet |
| 10,709,398 B2 | 7/2020 | Schweizer |
| 10,713,801 B2 | 7/2020 | Jordan et al. |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare et al. |
| 10,748,319 B1 | 8/2020 | Tao et al. |
| 10,758,315 B2 | 9/2020 | Johnson et al. |
| 10,777,094 B1 | 9/2020 | Rao et al. |
| 10,777,315 B2 | 9/2020 | Zehavi et al. |
| 10,781,482 B2 | 9/2020 | Gubatayao et al. |
| 10,792,110 B2 | 10/2020 | Leung et al. |
| 10,799,145 B2 | 10/2020 | West et al. |
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat et al. |
| 10,818,101 B2 | 10/2020 | Gallop et al. |
| 10,818,199 B2 | 10/2020 | Buras et al. |
| 10,825,563 B2 | 11/2020 | Gibby et al. |
| 10,827,164 B2 | 11/2020 | Perreault et al. |
| 10,831,943 B2 | 11/2020 | Santarone et al. |
| 10,835,296 B2 | 11/2020 | Elimelech et al. |
| 10,838,206 B2 | 11/2020 | Fortin-Deschnes et al. |
| 10,839,629 B2 | 11/2020 | Jones et al. |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker et al. |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino et al. |
| 10,869,517 B1 | 12/2020 | Halpern |
| 10,869,727 B2 | 12/2020 | Yanof et al. |
| 10,872,472 B2 | 12/2020 | Watola et al. |
| 10,877,262 B1 | 12/2020 | Luxembourg |
| 10,877,296 B2 | 12/2020 | Lindsey et al. |
| 10,878,639 B2 | 12/2020 | Douglas et al. |
| 10,893,260 B2 | 1/2021 | Trail et al. |
| 10,895,742 B2 | 1/2021 | Schneider et al. |
| 10,895,743 B2 | 1/2021 | Dausmann |
| 10,895,906 B2 | 1/2021 | West et al. |
| 10,898,151 B2 | 1/2021 | Harding et al. |
| 10,908,420 B2 | 2/2021 | Lee et al. |
| 10,921,595 B2 | 2/2021 | Rakshit et al. |
| 10,921,613 B2 | 2/2021 | Gupta et al. |
| 10,928,321 B2 | 2/2021 | Rawle |
| 10,928,638 B2 | 2/2021 | Ninan et al. |
| 10,929,670 B1 | 2/2021 | Troy et al. |
| 10,935,815 B1 | 3/2021 | Castaeda |
| 10,935,816 B2 | 3/2021 | Ban et al. |
| 10,936,537 B2 | 3/2021 | Huston |
| 10,939,973 B2 | 3/2021 | Dimaio et al. |
| 10,939,977 B2 | 3/2021 | Messinger et al. |
| 10,941,933 B2 | 3/2021 | Ferguson |
| 10,946,108 B2 | 3/2021 | Zhang et al. |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,969,587 B2 | 4/2021 | McDowall et al. |
| 10,993,754 B2 | 5/2021 | Kuntz et al. |
| 11,000,335 B2 | 5/2021 | Dorman |
| 11,002,994 B2 | 5/2021 | Jiang et al. |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti et al. |
| 11,013,573 B2 | 5/2021 | Chang |
| 11,013,900 B2 | 5/2021 | Malek et al. |
| 11,016,302 B2 | 5/2021 | Freeman et al. |
| 11,019,988 B2 | 6/2021 | Fiebel et al. |
| 11,027,027 B2 | 6/2021 | Manning et al. |
| 11,029,147 B2 | 6/2021 | Abovitz et al. |

(56) References Cited

U.S. PATENT DOCUMENTS

| | | |
|---|---|---|
| 11,030,809 B2 | 6/2021 | Wang |
| 11,041,173 B2 | 6/2021 | Zhang et al. |
| 11,045,663 B2 | 6/2021 | Mori et al. |
| 11,049,293 B2 | 6/2021 | Chae et al. |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour et al. |
| 11,067,387 B2 | 7/2021 | Marell et al. |
| 11,071,497 B2 | 7/2021 | Hallack et al. |
| 11,079,596 B2 | 8/2021 | Hua et al. |
| 11,087,039 B2 | 8/2021 | Duff et al. |
| 11,090,019 B2 | 8/2021 | Siemionow et al. |
| 11,097,129 B2 | 8/2021 | Sakata et al. |
| 11,099,376 B1 | 8/2021 | Steier et al. |
| 11,103,320 B2 | 8/2021 | Leboeuf et al. |
| D930,162 S | 9/2021 | Cremer et al. |
| 11,109,762 B1 | 9/2021 | Steier et al. |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford et al. |
| 11,135,016 B2 | 10/2021 | Frielinghaus et al. |
| 11,137,610 B1 | 10/2021 | Kessler et al. |
| 11,141,221 B2 | 10/2021 | Hobeika et al. |
| 11,153,549 B2 | 10/2021 | Casas |
| 11,153,555 B1 | 10/2021 | Healy et al. |
| 11,163,176 B2 | 11/2021 | Karafin et al. |
| 11,164,324 B2 | 11/2021 | Liu et al. |
| 11,166,006 B2 | 11/2021 | Hegyi |
| 11,169,380 B2 | 11/2021 | Manly et al. |
| 11,172,990 B2 | 11/2021 | Lang |
| 11,179,136 B2 | 11/2021 | Kohli et al. |
| 11,180,557 B2 | 11/2021 | Noelle |
| 11,181,747 B1 | 11/2021 | Kessler et al. |
| 11,185,891 B2 | 11/2021 | Cousins et al. |
| 11,187,907 B2 | 11/2021 | Osterman et al. |
| 11,202,682 B2 | 12/2021 | Staunton et al. |
| 11,207,150 B2 | 12/2021 | Healy et al. |
| 11,217,028 B2 | 1/2022 | Jones et al. |
| 11,224,483 B2 | 1/2022 | Steinberg et al. |
| 11,224,763 B2 | 1/2022 | Takahashi et al. |
| 11,227,417 B2 | 1/2022 | Berlinger et al. |
| 11,231,787 B2 | 1/2022 | Isaacs et al. |
| 11,243,404 B2 | 2/2022 | McDowall et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao et al. |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt et al. |
| 11,284,846 B2 | 3/2022 | Graumann et al. |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier et al. |
| 11,308,663 B2 | 4/2022 | Alhrishy et al. |
| 11,311,341 B2 | 4/2022 | Lang |
| 11,317,973 B2 | 5/2022 | Calloway et al. |
| 11,337,763 B2 | 5/2022 | Choi |
| 11,348,257 B2 | 5/2022 | Lang |
| 11,350,072 B1 | 5/2022 | Quiles Casas |
| 11,350,965 B2 | 6/2022 | Yilmaz et al. |
| 11,351,006 B2 | 6/2022 | Aferzon et al. |
| 11,354,813 B2 | 6/2022 | Piat et al. |
| 11,360,315 B2 | 6/2022 | Tu et al. |
| 11,373,342 B2 | 6/2022 | Stafford et al. |
| 11,382,699 B2 | 7/2022 | Wassall et al. |
| 11,382,700 B2 | 7/2022 | Calloway et al. |
| 11,382,712 B2 | 7/2022 | Elimelech et al. |
| 11,382,713 B2 | 7/2022 | Healy et al. |
| 11,389,252 B2 | 7/2022 | Gera et al. |
| 11,393,229 B2 | 7/2022 | Zhou et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,412,202 B2 | 8/2022 | Hegyi |
| 11,423,554 B2 | 8/2022 | Borsdorf et al. |
| 11,430,203 B2 | 8/2022 | Navab et al. |
| 11,432,828 B1 | 9/2022 | Lang |
| 11,432,931 B2 | 9/2022 | Lang |
| 11,443,428 B2 | 9/2022 | Petersen et al. |
| 11,443,431 B2 | 9/2022 | Flossmann et al. |
| 11,452,568 B2 | 9/2022 | Lang |
| 11,452,570 B2 | 9/2022 | Tolkowsky |
| 11,460,915 B2 | 10/2022 | Frielinghaus et al. |
| 11,461,936 B2 | 10/2022 | Freeman et al. |
| 11,461,983 B2 | 10/2022 | Jones et al. |
| 11,464,580 B2 | 10/2022 | Kemp et al. |
| 11,464,581 B2 | 10/2022 | Calloway |
| 11,475,625 B1 | 10/2022 | Douglas |
| 11,478,214 B2 | 10/2022 | Siewerdsen et al. |
| 11,483,532 B2 | 10/2022 | Quiles Casas |
| 11,488,021 B2 | 11/2022 | Sun et al. |
| 11,490,986 B2 | 11/2022 | BEn-Yishai |
| 11,510,750 B2 | 11/2022 | Dulin et al. |
| 11,513,358 B2 | 11/2022 | McDowall et al. |
| 11,527,002 B2 | 12/2022 | Govari |
| 11,528,393 B2 | 12/2022 | Garofolo et al. |
| 11,544,031 B2 | 1/2023 | Harviainen |
| 11,573,420 B2 | 2/2023 | Sarma et al. |
| 11,589,927 B2 | 2/2023 | Oezbek et al. |
| 11,627,924 B2 | 4/2023 | Alexandroni et al. |
| 11,644,675 B2 | 5/2023 | Manly et al. |
| 11,648,016 B2 | 5/2023 | Hathaway et al. |
| 11,651,499 B2 | 5/2023 | Wang et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,686,947 B2 | 6/2023 | Loyola et al. |
| 11,699,236 B2 | 7/2023 | Avital et al. |
| 11,712,582 B2 | 8/2023 | Miyazaki et al. |
| 11,715,210 B2 | 8/2023 | Haslam et al. |
| 11,719,941 B2 | 8/2023 | Russell |
| 11,730,389 B2 | 8/2023 | Farshad et al. |
| 11,733,516 B2 | 8/2023 | Edwin et al. |
| 11,734,901 B2 | 8/2023 | Jones et al. |
| 11,744,657 B2 | 9/2023 | Leboeuf et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,808,943 B2 | 11/2023 | Robaina et al. |
| 11,815,683 B2 | 11/2023 | Sears et al. |
| 11,826,111 B2 | 11/2023 | Mahfouz |
| 11,832,886 B2 | 12/2023 | Dorman |
| 11,838,493 B2 | 12/2023 | Healy et al. |
| 11,839,433 B2 | 12/2023 | Schaewe et al. |
| 11,839,501 B2 | 12/2023 | Takahashi et al. |
| 11,864,934 B2 | 1/2024 | Junio et al. |
| 11,885,752 B2 | 1/2024 | St-Aubin et al. |
| 11,892,647 B2 | 2/2024 | Hung et al. |
| 11,896,445 B2 | 2/2024 | Gera et al. |
| 11,900,620 B2 | 2/2024 | Lalys et al. |
| 11,914,155 B2 | 2/2024 | Zhu et al. |
| 11,918,310 B1 | 3/2024 | Roh et al. |
| 11,922,631 B2 | 3/2024 | Haslam et al. |
| 11,941,814 B2 | 3/2024 | Crawford et al. |
| 11,944,508 B1 | 4/2024 | Cowin et al. |

(56) References Cited

U.S. PATENT DOCUMENTS

| | | |
|---|---|---|
| 11,948,265 B2 | 4/2024 | Gibby et al. |
| 11,950,968 B2 | 4/2024 | Wiggermann |
| 11,957,420 B2 | 4/2024 | Lang |
| 11,961,193 B2 | 4/2024 | Pelzl et al. |
| 11,963,723 B2 | 4/2024 | Vilsmeier et al. |
| 11,972,582 B2 | 4/2024 | Yan et al. |
| 11,974,819 B2 | 5/2024 | Finley et al. |
| 11,974,887 B2 | 5/2024 | Elimelech et al. |
| 11,977,232 B2 | 5/2024 | Wu et al. |
| 11,980,429 B2 | 5/2024 | Wolf et al. |
| 11,980,506 B2 | 5/2024 | Wolf et al. |
| 11,980,507 B2 | 5/2024 | Elimelech et al. |
| 11,980,508 B2 | 5/2024 | Elimelech et al. |
| 11,983,824 B2 | 5/2024 | Avisar et al. |
| 12,002,171 B2 | 6/2024 | Jones et al. |
| 12,010,285 B2 | 6/2024 | Quiles Casas |
| 12,014,497 B2 | 6/2024 | Hong et al. |
| 12,019,314 B1 | 6/2024 | Steines et al. |
| 12,026,897 B2 | 7/2024 | Frantz et al. |
| 12,033,322 B2 | 7/2024 | Laaksonen et al. |
| 12,044,856 B2 | 7/2024 | Gera et al. |
| 12,044,858 B2 | 7/2024 | Gera et al. |
| 12,053,247 B1 | 8/2024 | Chiou |
| 12,056,830 B2 | 8/2024 | Cvetko et al. |
| 12,059,281 B2 | 8/2024 | Weingarten et al. |
| 12,063,338 B2 | 8/2024 | Quiles Casas |
| 12,063,345 B2 | 8/2024 | Benishti et al. |
| 12,069,233 B2 | 8/2024 | Benishti et al. |
| 12,076,158 B2 | 9/2024 | Geiger et al. |
| 12,076,196 B2 | 9/2024 | Elimelech et al. |
| 12,079,385 B2 | 9/2024 | Ben-Yishai et al. |
| 12,112,483 B2 | 10/2024 | Grady et al. |
| 12,114,933 B2 | 10/2024 | Seo et al. |
| 12,115,028 B2 | 10/2024 | Dulin et al. |
| 12,127,800 B2 | 10/2024 | Qian et al. |
| 12,133,772 B2 | 11/2024 | Calloway et al. |
| 12,136,176 B2 | 11/2024 | Spaas et al. |
| 12,142,365 B2 | 11/2024 | Kaethner et al. |
| 12,150,821 B2 | 11/2024 | Gera et al. |
| 12,178,666 B2 | 12/2024 | Wolf et al. |
| 12,186,028 B2 | 1/2025 | Gera et al. |
| 12,201,384 B2 | 1/2025 | Wolf et al. |
| 12,206,837 B2 | 1/2025 | Benishti et al. |
| 12,239,385 B2 | 3/2025 | Wolf et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley et al. |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0152955 A1 | 8/2004 | McGinley et al. |
| 2004/0171930 A1 | 9/2004 | Grimm et al. |
| 2004/0238732 A1 | 12/2004 | State et al. |
| 2005/0017972 A1 | 1/2005 | Poole et al. |
| 2005/0024586 A1 | 2/2005 | Teiwes et al. |
| 2005/0119639 A1 | 6/2005 | McCombs et al. |
| 2005/0154296 A1 | 7/2005 | Lechner et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1 | 12/2005 | Tuma et al. |
| 2006/0072124 A1 | 4/2006 | Smetak et al. |
| 2006/0134198 A1 | 6/2006 | Tawa et al. |
| 2006/0147100 A1 | 7/2006 | Fitzpatrick |
| 2006/0176242 A1 | 8/2006 | Jaramaz et al. |
| 2006/0241760 A1 | 10/2006 | Randall et al. |
| 2007/0018975 A1 | 1/2007 | Chuanggui et al. |
| 2007/0058261 A1 | 3/2007 | Sugihara et al. |
| 2007/0100325 A1 | 5/2007 | Jutras et al. |
| 2007/0183041 A1 | 8/2007 | McCloy et al. |
| 2007/0233371 A1 | 10/2007 | Stoschek et al. |
| 2007/0273610 A1 | 11/2007 | Baillot |
| 2008/0002809 A1 | 1/2008 | Bodduluri |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu et al. |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0005961 A1 | 1/2009 | Grabowski et al. |
| 2009/0018437 A1 | 1/2009 | Cooke |
| 2009/0024127 A1 | 1/2009 | Lechner et al. |
| 2009/0036902 A1 | 2/2009 | DiMaio et al. |
| 2009/0062869 A1 | 3/2009 | Claverie et al. |
| 2009/0099445 A1 | 4/2009 | Burger |
| 2009/0123452 A1 | 5/2009 | Madison |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1* | 3/2010 | Maier-Hein ............ A61B 6/12 600/426 |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0138939 A1 | 6/2010 | Bentzon et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0125159 A1 | 5/2011 | Hanson et al. |
| 2011/0125160 A1 | 5/2011 | Bagga et al. |
| 2011/0216060 A1 | 9/2011 | Weising et al. |
| 2011/0245625 A1 | 10/2011 | Trovato et al. |
| 2011/0248064 A1 | 10/2011 | Marczyk |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0238609 A1 | 9/2012 | Srivastava et al. |
| 2012/0245645 A1 | 9/2012 | Hanson et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao et al. |
| 2013/0195338 A1 | 8/2013 | Xu et al. |
| 2013/0209953 A1 | 8/2013 | Arlinsky et al. |
| 2013/0212453 A1 | 8/2013 | Gudai et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1* | 9/2013 | Maier-Hein ......... A61B 90/361 600/476 |
| 2013/0249787 A1 | 9/2013 | Morimoto |

(56) References Cited

U.S. PATENT DOCUMENTS

| | | |
|---|---|---|
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278631 A1 | 10/2013 | Border et al. |
| 2013/0278635 A1 | 10/2013 | Maggiore |
| 2013/0300637 A1 | 11/2013 | Smits et al. |
| 2013/0300760 A1 | 11/2013 | Sugano et al. |
| 2013/0342571 A1 | 12/2013 | Kinnebrew et al. |
| 2013/0345718 A1 | 12/2013 | Crawford et al. |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0105912 A1 | 4/2014 | Noelle |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0288413 A1 | 9/2014 | Hwang et al. |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1* | 11/2014 | Reiter ............... A61B 1/3132 600/111 |
| 2014/0340286 A1 | 11/2014 | Machida et al. |
| 2014/0361956 A1 | 12/2014 | Mikhailov et al. |
| 2014/0371728 A1 | 12/2014 | Vaughn |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Laor |
| 2015/0148847 A1 | 5/2015 | Moskowitz et al. |
| 2015/0150641 A1 | 6/2015 | Daon et al. |
| 2015/0182293 A1 | 7/2015 | Yang et al. |
| 2015/0192776 A1 | 7/2015 | Lee et al. |
| 2015/0209119 A1 | 7/2015 | Theodore et al. |
| 2015/0230873 A1 | 8/2015 | Kubiak et al. |
| 2015/0230893 A1 | 8/2015 | Huwais |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winne et al. |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0015878 A1 | 1/2016 | Graham et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang et al. |
| 2016/0163045 A1 | 6/2016 | Penney et al. |
| 2016/0175064 A1 | 6/2016 | Steinle et al. |
| 2016/0178910 A1 | 6/2016 | Giudicelli et al. |
| 2016/0191887 A1 | 6/2016 | Casas |
| 2016/0223822 A1 | 8/2016 | Harrison et al. |
| 2016/0228033 A1 | 8/2016 | Rossner |
| 2016/0246059 A1 | 8/2016 | Halpin et al. |
| 2016/0249989 A1 | 9/2016 | Devam et al. |
| 2016/0256223 A1 | 9/2016 | Haimerl et al. |
| 2016/0275684 A1 | 9/2016 | Elenbaas et al. |
| 2016/0297315 A1 | 10/2016 | Gonzalez et al. |
| 2016/0302870 A1 | 10/2016 | Wilkinson et al. |
| 2016/0324580 A1* | 11/2016 | Esterberg ............... A61B 34/10 |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0065364 A1 | 3/2017 | Schuh et al. |
| 2017/0068119 A1 | 3/2017 | Antaki et al. |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0148215 A1 | 5/2017 | Aksoy et al. |
| 2017/0164919 A1 | 6/2017 | Lavallee et al. |
| 2017/0164920 A1 | 6/2017 | Lavallee et al. |
| 2017/0172755 A1 | 6/2017 | Suh et al. |
| 2017/0178375 A1 | 6/2017 | Benishti et al. |
| 2017/0220224 A1 | 8/2017 | Kodali et al. |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0318235 A1 | 11/2017 | Schneider et al. |
| 2017/0322950 A1 | 11/2017 | Han et al. |
| 2017/0348055 A1 | 12/2017 | Salcedo et al. |
| 2017/0348061 A1 | 12/2017 | Joshi et al. |
| 2017/0366773 A1* | 12/2017 | Kiraly ............... A61B 1/00006 |
| 2017/0367766 A1 | 12/2017 | Mahfouz |
| 2017/0367771 A1 | 12/2017 | Tako et al. |
| 2017/0372477 A1 | 12/2017 | Penney et al. |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0071029 A1 | 3/2018 | Srimohanarajah et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0116741 A1 | 5/2018 | Garcia et al. |
| 2018/0117150 A1 | 5/2018 | O'Dwyer et al. |
| 2018/0120106 A1 | 5/2018 | Sato |
| 2018/0133871 A1 | 5/2018 | Farmer |
| 2018/0143442 A1 | 5/2018 | Gupta |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1* | 7/2018 | Gregerson ............ A61B 5/742 |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |

(56) References Cited

U.S. PATENT DOCUMENTS

| | | |
|---|---|---|
| 2018/0262743 A1 | 9/2018 | Casas |
| 2018/0303558 A1 | 10/2018 | Thomas |
| 2018/0311011 A1 | 11/2018 | Van et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper et al. |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios et al. |
| 2019/0142519 A1 | 5/2019 | Siemionow et al. |
| 2019/0144443 A1 | 5/2019 | Jackson et al. |
| 2019/0175228 A1 | 6/2019 | Elimelech et al. |
| 2019/0192226 A1 | 6/2019 | Lang |
| 2019/0192230 A1 | 6/2019 | Siemionow et al. |
| 2019/0200894 A1 | 7/2019 | Jung et al. |
| 2019/0201106 A1 | 7/2019 | Siemionow et al. |
| 2019/0205606 A1 | 7/2019 | Zhou et al. |
| 2019/0216537 A1 | 7/2019 | Eltorai et al. |
| 2019/0251692 A1 | 8/2019 | Schmidt-Richberg et al. |
| 2019/0251694 A1 | 8/2019 | Han et al. |
| 2019/0254753 A1 | 8/2019 | Johnson et al. |
| 2019/0273916 A1 | 9/2019 | Benishti et al. |
| 2019/0310481 A1 | 10/2019 | Blum et al. |
| 2019/0324365 A1 | 10/2019 | De et al. |
| 2019/0333480 A1 | 10/2019 | Lang |
| 2019/0369660 A1 | 12/2019 | Wen et al. |
| 2019/0369717 A1 | 12/2019 | Frielinghaus et al. |
| 2019/0378276 A1 | 12/2019 | Flossmann et al. |
| 2019/0387351 A1 | 12/2019 | Lyren et al. |
| 2020/0015895 A1 | 1/2020 | Frielinghaus et al. |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0059640 A1 | 2/2020 | Browd et al. |
| 2020/0078100 A1 | 3/2020 | Weinstein et al. |
| 2020/0085511 A1* | 3/2020 | Oezbek ................ A61B 34/10 |
| 2020/0088997 A1 | 3/2020 | Lee et al. |
| 2020/0100847 A1 | 4/2020 | Siegler et al. |
| 2020/0117025 A1 | 4/2020 | Sauer |
| 2020/0129058 A1 | 4/2020 | Li et al. |
| 2020/0129136 A1 | 4/2020 | Harding et al. |
| 2020/0129262 A1 | 4/2020 | Verard et al. |
| 2020/0129264 A1 | 4/2020 | Oativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene et al. |
| 2020/0151507 A1 | 5/2020 | Siemionow et al. |
| 2020/0156259 A1 | 5/2020 | Ruiz et al. |
| 2020/0159313 A1 | 5/2020 | Gibby et al. |
| 2020/0163723 A1 | 5/2020 | Wolf et al. |
| 2020/0163739 A1 | 5/2020 | Messinger et al. |
| 2020/0178916 A1 | 6/2020 | Lalys et al. |
| 2020/0184638 A1 | 6/2020 | Meglan et al. |
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent et al. |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei et al. |
| 2020/0275988 A1 | 9/2020 | Johnson et al. |
| 2020/0281554 A1 | 9/2020 | Trini et al. |
| 2020/0286222 A1 | 9/2020 | Essenreiter et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza et al. |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler et al. |
| 2020/0341283 A1 | 10/2020 | McCracken et al. |
| 2020/0352655 A1 | 11/2020 | Freese |
| 2020/0355927 A1 | 11/2020 | Marcellin-Dibon et al. |
| 2020/0360091 A1 | 11/2020 | Murray et al. |
| 2020/0360105 A1 | 11/2020 | Frey et al. |
| 2020/0375666 A1 | 12/2020 | Stephen |
| 2020/0377493 A1 | 12/2020 | Heiser et al. |
| 2020/0377956 A1 | 12/2020 | Vogelstein et al. |
| 2020/0386982 A1 | 12/2020 | Luxembourg |
| 2020/0388075 A1 | 12/2020 | Kazanzides et al. |
| 2020/0389425 A1 | 12/2020 | Bhatia et al. |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani et al. |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar et al. |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu et al. |
| 2021/0049825 A1 | 2/2021 | Wheelwright et al. |
| 2021/0052348 A1 | 2/2021 | Stifter et al. |
| 2021/0056687 A1 | 2/2021 | Hibbard et al. |
| 2021/0065911 A1 | 3/2021 | Goel et al. |
| 2021/0077195 A1 | 3/2021 | Saeidi et al. |
| 2021/0077210 A1 | 3/2021 | Itkowitz et al. |
| 2021/0080751 A1 | 3/2021 | Lindsey et al. |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quaid et al. |
| 2021/0093417 A1 | 4/2021 | Liu |
| 2021/0104055 A1 | 4/2021 | Ni et al. |
| 2021/0107923 A1 | 4/2021 | Jackson et al. |
| 2021/0109349 A1 | 4/2021 | Schneider et al. |
| 2021/0109373 A1 | 4/2021 | Loo et al. |
| 2021/0110517 A1 | 4/2021 | Flohr et al. |
| 2021/0113269 A1 | 4/2021 | Vilsmeier et al. |
| 2021/0113293 A9 | 4/2021 | Silva et al. |
| 2021/0121238 A1 | 4/2021 | Palushi et al. |
| 2021/0137634 A1 | 5/2021 | Lang |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing et al. |
| 2021/0165207 A1 | 6/2021 | Peyman |
| 2021/0169504 A1 | 6/2021 | Brown |
| 2021/0169578 A1 | 6/2021 | Calloway et al. |

(56) References Cited

U.S. PATENT DOCUMENTS

| | | |
|---|---|---|
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zhang et al. |
| 2021/0225006 A1 | 7/2021 | Grady et al. |
| 2021/0227791 A1 | 7/2021 | De et al. |
| 2021/0231301 A1 | 7/2021 | Hikmet et al. |
| 2021/0235061 A1 | 7/2021 | Hegyi |
| 2021/0248822 A1 | 8/2021 | Choi et al. |
| 2021/0274281 A1 | 9/2021 | Zhang et al. |
| 2021/0278675 A1 | 9/2021 | Klug et al. |
| 2021/0282887 A1 | 9/2021 | Wiggermann |
| 2021/0290046 A1 | 9/2021 | Nazareth et al. |
| 2021/0290336 A1 | 9/2021 | Wang |
| 2021/0290394 A1 | 9/2021 | Mahfouz |
| 2021/0295108 A1 | 9/2021 | Bar |
| 2021/0295512 A1 | 9/2021 | Knoplioch et al. |
| 2021/0298795 A1 | 9/2021 | Bowling et al. |
| 2021/0298835 A1 | 9/2021 | Wang |
| 2021/0306599 A1 | 9/2021 | Pierce |
| 2021/0311322 A1 | 10/2021 | Belanger et al. |
| 2021/0314502 A1 | 10/2021 | Liu |
| 2021/0315636 A1 | 10/2021 | Akbarian et al. |
| 2021/0315662 A1 | 10/2021 | Freeman et al. |
| 2021/0325684 A1 | 10/2021 | Ninan et al. |
| 2021/0332447 A1 | 10/2021 | Lubelski et al. |
| 2021/0333561 A1 | 10/2021 | Oh et al. |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev et al. |
| 2021/0364802 A1 | 11/2021 | Uchiyama et al. |
| 2021/0369226 A1 | 12/2021 | Siemionow et al. |
| 2021/0371413 A1 | 12/2021 | Thurston et al. |
| 2021/0373333 A1 | 12/2021 | Moon |
| 2021/0373344 A1 | 12/2021 | Loyola et al. |
| 2021/0378757 A1 | 12/2021 | Bay et al. |
| 2021/0382310 A1 | 12/2021 | Freeman et al. |
| 2021/0386482 A1 | 12/2021 | Gera et al. |
| 2021/0389590 A1 | 12/2021 | Freeman et al. |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0125496 A1 | 4/2022 | Lpez et al. |
| 2022/0133484 A1 | 5/2022 | Lang |
| 2022/0142730 A1 | 5/2022 | Wolf et al. |
| 2022/0155861 A1 | 5/2022 | Myung et al. |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0257206 A1 | 8/2022 | Hartley et al. |
| 2022/0269077 A1 | 8/2022 | Adema et al. |
| 2022/0270263 A1 | 8/2022 | Junio |
| 2022/0287676 A1 | 9/2022 | Steines et al. |
| 2022/0292786 A1 | 9/2022 | Pelzl et al. |
| 2022/0295033 A1 | 9/2022 | Quiles Casas |
| 2022/0296315 A1 | 9/2022 | Sokhanvar et al. |
| 2022/0304768 A1 | 9/2022 | Elimelech et al. |
| 2022/0351385 A1 | 11/2022 | Finley et al. |
| 2022/0353487 A1 | 11/2022 | Hegyi |
| 2022/0358759 A1 | 11/2022 | Cork et al. |
| 2022/0370152 A1 | 11/2022 | Lavallee et al. |
| 2022/0387130 A1 | 12/2022 | Spaas et al. |
| 2022/0392085 A1 | 12/2022 | Finley et al. |
| 2022/0397750 A1 | 12/2022 | Zhou et al. |
| 2022/0398752 A1 | 12/2022 | Yoon et al. |
| 2022/0398755 A1 | 12/2022 | Herrmann |
| 2022/0405935 A1 | 12/2022 | Flossmann et al. |
| 2023/0004013 A1 | 1/2023 | McCracken et al. |
| 2023/0009793 A1 | 1/2023 | Gera et al. |
| 2023/0025480 A1 | 1/2023 | Kemp et al. |
| 2023/0027801 A1 | 1/2023 | Qian et al. |
| 2023/0032731 A1 | 2/2023 | Hrndler et al. |
| 2023/0034189 A1 | 2/2023 | Gera et al. |
| 2023/0050636 A1 | 2/2023 | Yanof et al. |
| 2023/0053120 A1 | 2/2023 | Jamali et al. |
| 2023/0073041 A1 | 3/2023 | Samadani et al. |
| 2023/0085387 A1 | 3/2023 | Jones et al. |
| 2023/0087783 A1 | 3/2023 | Dulin et al. |
| 2023/0100078 A1 | 3/2023 | Toporek et al. |
| 2023/0123621 A1 | 4/2023 | Joshi et al. |
| 2023/0126207 A1 | 4/2023 | Wang |
| 2023/0129056 A1 | 4/2023 | Hemingway et al. |
| 2023/0131515 A1 | 4/2023 | Oezbek et al. |
| 2023/0149083 A1 | 5/2023 | Lin et al. |
| 2023/0162493 A1 | 5/2023 | Worrell et al. |
| 2023/0165640 A1 | 6/2023 | Dulin et al. |
| 2023/0169659 A1 | 6/2023 | Chen et al. |
| 2023/0196582 A1 | 6/2023 | Grady et al. |
| 2023/0200917 A1 | 6/2023 | Calloway et al. |
| 2023/0236426 A1 | 7/2023 | Manly et al. |
| 2023/0236427 A1 | 7/2023 | Jiannyuh |
| 2023/0245784 A1 | 8/2023 | Crawford et al. |
| 2023/0260142 A1 | 8/2023 | Chatterjee et al. |
| 2023/0290037 A1* | 9/2023 | Tasse ................. G06T 15/04 345/420 |
| 2023/0295302 A1* | 9/2023 | Bhagavatheeswaran ................... C07K 16/2818 424/143.1 |
| 2023/0306590 A1 | 9/2023 | Jazdzyk et al. |
| 2023/0316550 A1 | 10/2023 | Hiasa |
| 2023/0326011 A1 | 10/2023 | Cutforth et al. |
| 2023/0326027 A1 | 10/2023 | Wahrenberg |
| 2023/0329799 A1 | 10/2023 | Gera et al. |
| 2023/0329801 A1 | 10/2023 | Elimelech et al. |
| 2023/0334664 A1 | 10/2023 | Lu et al. |
| 2023/0335261 A1 | 10/2023 | Reicher et al. |
| 2023/0359043 A1 | 11/2023 | Russell |
| 2023/0363832 A1 | 11/2023 | Mosadegh et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377171 A1 | 11/2023 | Hasler et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386022 A1 | 11/2023 | Tan et al. |
| 2023/0386067 A1 | 11/2023 | De et al. |
| 2023/0386153 A1 | 11/2023 | Rybnikov et al. |
| 2023/0389991 A1 | 12/2023 | Glaser et al. |
| 2023/0394791 A1 | 12/2023 | Wang et al. |
| 2023/0397349 A1 | 12/2023 | Capelli et al. |
| 2023/0397957 A1 | 12/2023 | Crawford et al. |
| 2023/0419496 A1 | 12/2023 | Wuelker et al. |
| 2023/0420114 A1 | 12/2023 | Scholler et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |

(56) References Cited

U.S. PATENT DOCUMENTS

| | | |
|---|---|---|
| 2024/0041530 A1 | 2/2024 | Lang |
| 2024/0041558 A1 | 2/2024 | Siewerdsen et al. |
| 2024/0045491 A1 | 2/2024 | Sourov |
| 2024/0058064 A1 | 2/2024 | Weiser et al. |
| 2024/0062387 A1 | 2/2024 | Frantz et al. |
| 2024/0103271 A1 | 3/2024 | Zare Seisan |
| 2024/0103282 A1 | 3/2024 | Law et al. |
| 2024/0111163 A1 | 4/2024 | Law et al. |
| 2024/0122560 A1 | 4/2024 | Junio et al. |
| 2024/0126087 A1 | 4/2024 | Gera et al. |
| 2024/0127559 A1 | 4/2024 | Rybnikov et al. |
| 2024/0127578 A1 | 4/2024 | Hiasa |
| 2024/0129451 A1 | 4/2024 | Healy et al. |
| 2024/0130826 A1 | 4/2024 | Elimelech et al. |
| 2024/0134206 A1 | 4/2024 | Gera et al. |
| 2024/0144497 A1 | 5/2024 | Cvetko et al. |
| 2024/0156532 A1 | 5/2024 | Weiman et al. |
| 2024/0177445 A1 | 5/2024 | Galeotti et al. |
| 2024/0177458 A1 | 5/2024 | Zhang et al. |
| 2024/0180634 A1 | 6/2024 | Mikus |
| 2024/0184119 A1 | 6/2024 | Lee et al. |
| 2024/0185509 A1 | 6/2024 | Kovler et al. |
| 2024/0202926 A1 | 6/2024 | Crawford et al. |
| 2024/0202927 A1 | 6/2024 | Haslam et al. |
| 2024/0212111 A1 | 6/2024 | Genghi et al. |
| 2024/0233131 A1 | 7/2024 | Westerhoff et al. |
| 2024/0245463 A1 | 7/2024 | Vilsmeier et al. |
| 2024/0245474 A1 | 7/2024 | Weiman et al. |
| 2024/0248530 A1 | 7/2024 | Gibby et al. |
| 2024/0252252 A1 | 8/2024 | Lang |
| 2024/0261036 A1 | 8/2024 | Finley et al. |
| 2024/0261058 A1 | 8/2024 | Gera et al. |
| 2024/0265645 A1 | 8/2024 | Papar |
| 2024/0266033 A1 | 8/2024 | Freeman et al. |
| 2024/0268922 A1 | 8/2024 | Calloway et al. |
| 2024/0273740 A1 | 8/2024 | Gibby et al. |
| 2024/0281979 A1 | 8/2024 | Schrempf et al. |
| 2024/0296527 A1 | 9/2024 | Nett et al. |
| 2024/0303832 A1 | 9/2024 | Chen et al. |
| 2024/0307101 A1 | 9/2024 | Gera et al. |
| 2024/0312012 A1 | 9/2024 | Li et al. |
| 2024/0341853 A1 | 10/2024 | Gibby et al. |
| 2024/0341861 A1 | 10/2024 | Wolf et al. |
| 2024/0341910 A1 | 10/2024 | Wolf et al. |
| 2024/0341911 A1 | 10/2024 | Elimelech et al. |
| 2024/0355098 A1 | 10/2024 | Liu et al. |
| 2024/0374314 A1 | 11/2024 | Frey et al. |
| 2024/0377640 A1 | 11/2024 | Asaban et al. |
| 2024/0378708 A1 | 11/2024 | Kim et al. |
| 2024/0382283 A1 | 11/2024 | Kuhnert et al. |
| 2024/0386572 A1 | 11/2024 | Barasofsky et al. |
| 2024/0386682 A1 | 11/2024 | Cvetko et al. |
| 2024/0394883 A1 | 11/2024 | Liao et al. |
| 2024/0394985 A1 | 11/2024 | Hanlon et al. |
| 2024/0404065 A1 | 12/2024 | Gibbons et al. |
| 2024/0404106 A1 | 12/2024 | Wu et al. |
| 2024/0404180 A1 | 12/2024 | Kobayashi et al. |
| 2024/0420337 A1 | 12/2024 | Li et al. |
| 2024/0420592 A1 | 12/2024 | Stone et al. |
| 2024/0423724 A1 | 12/2024 | Wolf et al. |
| 2024/0423750 A1 | 12/2024 | Elimelech et al. |
| 2025/0020931 A1 | 1/2025 | Gera et al. |
| 2025/0049534 A1 | 2/2025 | Elimelech et al. |
| 2025/0090266 A1 | 3/2025 | Gera et al. |
| 2025/0114151 A1 | 4/2025 | Gera et al. |
| 2025/0114164 A1 | 4/2025 | Gera et al. |
| 2025/0114165 A1 | 4/2025 | Wolf et al. |

FOREIGN PATENT DOCUMENTS

| | | |
|---|---|---|
| CN | 101379412 A | 3/2009 |
| CN | 102740784 A | 10/2012 |
| CN | 102740789 A | 10/2012 |
| CN | 103106348 A | 5/2013 |
| CN | 103945780 A | 7/2014 |
| CN | 105310756 A | 2/2016 |
| CN | 109199563 A | 1/2019 |
| CN | 111915696 A | 11/2020 |
| CN | 112489047 A | 3/2021 |
| DE | 202004011567 U1 | 11/2004 |
| DE | 102004011567 A1 | 9/2005 |
| DE | 102014008153 A1 | 10/2014 |
| DE | 202022103168 U1 | 6/2022 |
| EP | 0933096 A2 | 8/1999 |
| EP | 1640750 A1 | 3/2006 |
| EP | 1757974 A1 | 2/2007 |
| EP | 2119397 A1 | 11/2009 |
| EP | 2134847 A2 | 12/2009 |
| EP | 2557998 A1 | 2/2013 |
| EP | 2823463 A1 | 1/2015 |
| EP | 2868277 A1 | 5/2015 |
| EP | 2891966 A1 | 7/2015 |
| EP | 2963616 A2 | 1/2016 |
| EP | 3028258 A1 | 6/2016 |
| EP | 3034607 A1 | 6/2016 |
| EP | 3037038 A1 | 6/2016 |
| EP | 3069318 A1 | 9/2016 |
| EP | 3076660 A1 | 10/2016 |
| EP | 3121789 A1 | 1/2017 |
| EP | 3123970 A1 | 2/2017 |
| EP | 2654749 B1 | 5/2017 |
| EP | 3175815 A1 | 6/2017 |
| EP | 3216416 A1 | 9/2017 |
| EP | 2032039 B1 | 10/2017 |
| EP | 3224376 A1 | 10/2017 |
| EP | 3247297 A1 | 11/2017 |
| EP | 3256213 A1 | 12/2017 |
| EP | 3306567 A1 | 4/2018 |
| EP | 3320874 A1 | 5/2018 |
| EP | 2030193 B1 | 7/2018 |
| EP | 2225723 B1 | 2/2019 |
| EP | 2619622 B1 | 2/2019 |
| EP | 2892558 B1 | 4/2019 |
| EP | 3494903 A1 | 6/2019 |
| EP | 2635299 B1 | 7/2019 |
| EP | 3505050 A1 | 7/2019 |
| EP | 2875149 B1 | 12/2019 |
| EP | 3593227 A1 | 1/2020 |
| EP | 3634294 A1 | 4/2020 |
| EP | 3206583 B1 | 9/2020 |
| EP | 3711700 A1 | 9/2020 |
| EP | 2625845 B1 | 3/2021 |
| EP | 3789965 A1 | 3/2021 |
| EP | 3858280 A1 | 8/2021 |
| EP | 3913423 A1 | 11/2021 |
| EP | 3952331 A1 | 2/2022 |
| EP | 3960235 A1 | 3/2022 |
| EP | 3635683 B1 | 7/2022 |
| EP | 3602492 B1 | 11/2022 |
| EP | 4173590 A1 | 5/2023 |
| EP | 3533031 B1 | 8/2023 |
| EP | 4252695 A1 | 10/2023 |
| EP | 3195257 B1 | 11/2023 |
| EP | 3405909 B1 | 11/2023 |
| EP | 4270313 A1 | 11/2023 |
| EP | 4287120 A1 | 12/2023 |
| EP | 3488381 B1 | 2/2024 |
| EP | 3834768 B1 | 2/2024 |
| EP | 3903714 B1 | 2/2024 |
| EP | 4336450 A1 | 3/2024 |
| EP | 3814984 B1 | 4/2024 |
| EP | 4115389 B1 | 4/2024 |
| EP | 3752981 B1 | 5/2024 |
| EP | 4375948 A1 | 5/2024 |
| EP | 4383203 A1 | 6/2024 |
| EP | 4459543 A1 | 11/2024 |
| EP | 4292045 B1 | 12/2024 |
| EP | 4298604 B1 | 12/2024 |
| GB | 2507314 A | 4/2014 |
| IL | 262864 A | 3/2019 |
| JP | 2004-237092 A | 8/2004 |
| JP | 2005-246059 A | 9/2005 |
| JP | 2008-507361 A | 3/2008 |
| JP | 2009-514571 A | 4/2009 |

(56) References Cited

FOREIGN PATENT DOCUMENTS

| | | |
|---|---|---|
| JP | 2021-525186 A | 9/2021 |
| KR | 10-2014-0120155 A | 10/2014 |
| WO | 03/34705 A2 | 4/2003 |
| WO | 2006/002559 A1 | 1/2006 |
| WO | 2007/051304 A1 | 5/2007 |
| WO | 2007/115826 A2 | 10/2007 |
| WO | 2008/103383 A1 | 8/2008 |
| WO | 2010/067267 A1 | 6/2010 |
| WO | 2010/074747 A1 | 7/2010 |
| WO | 2012/061537 A2 | 5/2012 |
| WO | 2012/101286 A1 | 8/2012 |
| WO | 2013/112554 A1 | 8/2013 |
| WO | 2014/014498 A1 | 1/2014 |
| WO | 2014/024188 A1 | 2/2014 |
| WO | 2014/037953 A2 | 3/2014 |
| WO | 2014/113455 A1 | 7/2014 |
| WO | 2014/125789 A1 | 8/2014 |
| WO | 2014/167563 A1 | 10/2014 |
| WO | 2014/174067 A1 | 10/2014 |
| WO | 2015/058816 A1 | 4/2015 |
| WO | 2015/061752 A1 | 4/2015 |
| WO | 2015/109145 A1 | 7/2015 |
| WO | 2016/151506 A1 | 9/2016 |
| WO | 2017/042171 A1 | 3/2017 |
| WO | 2018/052966 A1 | 3/2018 |
| WO | 2018/073452 A1 | 4/2018 |
| WO | 2018/200767 A1 | 11/2018 |
| WO | 2018/206086 A1 | 11/2018 |
| WO | 2019/083431 A1 | 5/2019 |
| WO | 2019/135209 A1 | 7/2019 |
| WO | 2019/135210 A1 | 7/2019 |
| WO | 2019/161477 A1 | 8/2019 |
| WO | 2019/195926 A1 | 10/2019 |
| WO | 2019/210353 A1 | 11/2019 |
| WO | 2019/211741 A1 | 11/2019 |
| WO | 2020/109903 A1 | 6/2020 |
| WO | 2020/109904 A1 | 6/2020 |
| WO | 2021/017019 A1 | 2/2021 |
| WO | 2021/019369 A1 | 2/2021 |
| WO | 2021/021979 A2 | 2/2021 |
| WO | 2021/023574 A1 | 2/2021 |
| WO | 2021/046455 A1 | 3/2021 |
| WO | 2021/048158 A1 | 3/2021 |
| WO | 2021/061459 A1 | 4/2021 |
| WO | 2021/062375 A1 | 4/2021 |
| WO | 2021/073743 A1 | 4/2021 |
| WO | 2021/087439 A1 | 5/2021 |
| WO | 2021/091980 A1 | 5/2021 |
| WO | 2021/112918 A1 | 6/2021 |
| WO | 2021/130564 A1 | 7/2021 |
| WO | 2021/137752 A1 | 7/2021 |
| WO | 2021/141887 A1 | 7/2021 |
| WO | 2021/145584 A1 | 7/2021 |
| WO | 2021/154076 A1 | 8/2021 |
| WO | 2021/183318 A2 | 9/2021 |
| WO | 2021/188757 A1 | 9/2021 |
| WO | 2021/255627 A1 | 12/2021 |
| WO | 2021/257897 A1 | 12/2021 |
| WO | 2021/258078 A1 | 12/2021 |
| WO | 2022/009233 A1 | 1/2022 |
| WO | 2022/053923 A1 | 3/2022 |
| WO | 2022/056010 A1 | 3/2022 |
| WO | 2022/079565 A1 | 4/2022 |
| WO | 2022/180624 A1 | 9/2022 |
| WO | 2023/003952 A1 | 1/2023 |
| WO | 2023/281395 A1 | 1/2023 |
| WO | 2023/007418 A1 | 2/2023 |
| WO | 2023/011924 A1 | 2/2023 |
| WO | 2023/021448 A1 | 2/2023 |
| WO | 2023/021450 A1 | 2/2023 |
| WO | 2023/021451 A1 | 2/2023 |
| WO | 2023/026229 A1 | 3/2023 |
| WO | 2023/047355 A1 | 3/2023 |
| WO | 2023/072887 A1 | 5/2023 |
| WO | 2023/088986 A1 | 5/2023 |
| WO | 2023/158878 A1 | 8/2023 |
| WO | 2023/159104 A2 | 8/2023 |
| WO | 2023/161848 A1 | 8/2023 |
| WO | 2023/163933 A1 | 8/2023 |
| WO | 2023/175244 A1 | 9/2023 |
| WO | 2023/186996 A1 | 10/2023 |
| WO | 2023/202909 A1 | 10/2023 |
| WO | 2023/205212 A1 | 10/2023 |
| WO | 2023/205896 A1 | 11/2023 |
| WO | 2023/209014 A1 | 11/2023 |
| WO | 2023/229415 A1 | 11/2023 |
| WO | 2023/232492 A1 | 12/2023 |
| WO | 2023/240912 A1 | 12/2023 |
| WO | 2024/001140 A1 | 1/2024 |
| WO | 2024/002620 A1 | 1/2024 |
| WO | 2024/013642 A2 | 1/2024 |
| WO | 2024/018368 A2 | 1/2024 |
| WO | 2024/046760 A1 | 3/2024 |
| WO | 2024/052136 A1 | 3/2024 |
| WO | 2024/077077 A1 | 4/2024 |
| WO | 2024/121060 A1 | 6/2024 |
| WO | 2024/132609 A1 | 6/2024 |
| WO | 2024/145341 A1 | 7/2024 |
| WO | 2024/160896 A1 | 8/2024 |
| WO | 2024/165508 A1 | 8/2024 |
| WO | 2024/173251 A1 | 8/2024 |
| WO | 2024/186811 A1 | 9/2024 |
| WO | 2024/226797 A1 | 10/2024 |
| WO | 2024/251344 A1 | 12/2024 |

OTHER PUBLICATIONS

International Search Report and Written Opinion received for PCT Patent Application No. PCT/IB2022/057733, dated Jan. 26, 2023, 14 pages.
U.S. Appl. No. 16/419,023 (U.S. Pat. No. 11,750,794, filed May 22, 2019, Combining Video-Based and Optic-Based Augmented Reality in a Near Eye Display.
U.S. Appl. No. 18/365,643, filed Aug. 4, 2023, Head-Mounted Augmented Reality Near Eye Display Device.
U.S. Appl. No. 18/365,650, filed Aug. 4, 2023, Systems for Facilitating Augmented Reality-Assisted Medical Procedures.
U.S. Appl. No. 18/365,590, filed Aug. 4, 2023, Registration of a Fiducial Marker for an Augmented Reality System.
U.S. Appl. No. 18/365,571, filed Aug. 4, 2023, Registration Marker for an Augmented Reality System.
U.S. Appl. No. 17/045,766, filed Oct. 7, 2020, Registration of a Fiducial Marker for an Augmented Reality System.
U.S. Appl. No. 16/524,258, filed Jul. 29, 2019, Fiducial Marker.
U.S. Appl. No. 17/827,710, filed May 29, 2022, Mirroring in Image Guided Surgery.
U.S. Appl. No. 16/200,144, filed Nov. 26, 2018, Tracking System for Image-Guided Surgery.
U.S. Appl. No. 18/044,380, filed Mar. 8, 2023, Universal Tool Adapter for Image-Guided Surgery.
U.S. Appl. No. 17/368,859, filed Jul. 7, 2021, Iliac Pin and Adapter.
U.S. Appl. No. 35/508,942 (U.S. Pat. No. D. 930,162, filed Feb. 13, 2020 (Sep. 7, 2021), Medical Headset.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Everysight, Installing your RX Adaptor, accessed Mar. 13, 2024 at https://support.everysight.com/hc/en-us/articles/115000984571-Installing-your-RX-Adaptor.
Everysight, Raptor User Manual, copyright 2017, in 46 pages.
Frames Direct, InSpatialRx Prescription Insert, Prescription Insert for Magic Leap 1, accessed Mar. 8, 2024 at https://www.framesdirect.com/inspatialrx-prescription-insert.html.
Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.

(56) References Cited

OTHER PUBLICATIONS

U.S. Appl. No. 15/896,102, U.S. Pat. No. 10,134,166, filed Feb 14, 2018, Nov. 20, 2018, Combining Video-Based and Optic-Based Augmented Reality In A Near Eye Display.
U.S. Appl. No. 16/159,740, U.S. Pat. No. 10,382,748, filed Oct. 15, 2018, Aug. 13, 2019, Combining Video-Based and Optic-Based Augmented Reality in a Near Eye Display.
U.S. Appl. No. 16/419,023, U.S. Pat. No. 11,750,794, filed May 22, 2019, Sep. 5, 2023, Combining Video-Based and Optic-Based Augmented Reality in a Near Eye Display.
U.S. Appl. No. 18/352,158, filed Jul. 13, 2023, Combining Video-Based and Optic-Based Augmented Reality in a Near Eye Display.
U.S. Appl. No. 18/365,643, U.S. Pat. No. 12,069,233, filed Aug. 4, 2023, Head-Mounted Augmented Reality Near Eye Display Device.
U.S. Appl. No. 18/365,650, U.S. Pat. No. 12,063,345, filed Aug. 4, 2023, Systems For Facilitating Augmented Reality-Assisted Medical Procedures.
U.S. Appl. No. 15/127,423, U.S. Pat. No. 9,928,629, filed Sep. 20, 2016, Mar. 27, 2018, Combining Video-Based and Optic-Based Augmented Reality in a Near Eye Display.
U.S. Appl. No. 16/120,480, U.S. Pat. No. 10,835,296, filed Sep. 4, 2018, Nov. 17, 2020, Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590, U.S. Pat. No. 11,980,508, filed Aug. 4, 2023, May 14, 2024, Registration of a Fiducial Marker for an Augmented Reality System.
U.S. Appl. No. 18/365,571, U.S. Pat. No. 11,974,887, filed Aug. 4, 2023, May 7, 2024, Registration Marker for an Augmented Reality System.
U.S. Appl. No. 18/632,588, filed Apr. 11, 2024, Registration of a Fiducial Marker for an Augmented Reality System.
U.S. Appl. No. 17/045,766, U.S. Pat. No. 11,980,507, filed Oct. 7, 2020, May 14, 2024, Registration of a Fiducial Marker for an Augmented Reality System.
U.S. Appl. No. 16/199,281, U.S. Pat. No. 10,939,977, filed Nov. 26, 2018, Mar. 9, 2021, Positioning Marker.
U.S. Appl. No. 16/524,258, U.S. Pat. No. 11,980,506, filed Jul. 29, 2019, May 14, 2024, Fiducial Marker.
U.S. Appl. No. 18/631,804, filed Apr. 10, 2024, Fiducial Marker.
U.S. Appl. No. 17/585,629, filed Jan. 27, 2022, Fiducial Marker.
U.S. Appl. No. 16/724,297, U.S. Pat. No. 11,382,712, filed Dec. 22, 2019, Jul. 12, 2022, Mirroring in Image Guided Surgery.
U.S. Appl. No. 17/827,710, U.S. Pat. No. 11,801,115, filed May 29, 2022, Oct. 31, 2023, Mirroring in Image Guided Surgery.
U.S. Appl. No. 18/352,181, filed Jul. 13, 2023, Mirroring in Image Guided Surgery.
U.S. Appl. No. 18/400,739, filed Dec. 29, 2023, Mirroring in Image Guided Surgery.
U.S. Appl. No. 18/780,095, filed Jul. 22, 2024, Mirroring in Image Guided Surgery.
U.S. Appl. No. 16/200,144, U.S. Pat. No. 11,766,296, filed Nov. 26, 2018, Sep. 26, 2023, Tracking System for Image-Guided Surgery.
U.S. Appl. No. 18/470,809, U.S. Pat. No. 11,980,429, filed Sep. 20, 2023, May 14, 2024, Tracking Methods for Image-Guided Surgery.
U.S. Appl. No. 18/631,877, filed Apr. 10, 2024, Tracking Systems and Methods for Image-Guided Surgery.
U.S. Appl. No. 17/015,199, filed Sep. 9, 2020, Universal Tool Adapter.
U.S. Appl. No. 18/598,965, filed Mar. 7, 2024, Universal Tool Adapter For Image Guide Surgery.
U.S. Appl. No. 18/044,380, filed Mar. 8, 2023, Universal Tool Adapter For Image-Guide Surgery.
U.S. Appl. No. 16/901,026, U.S. Pat. No. 11,389,252, filed Jun. 15, 2020, Jul. 19, 2022, Rotating Marker For Image Guided Surgery.
U.S. Appl. No. 18/008,980, filed Dec. 8, 2022, Rotating Marker.
U.S. Appl. No. 17/368,859, U.S. Pat. No. 11,896,445, filed Jul. 7, 2021, Feb. 13, 2024, Iliac Pin and Adapter.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 17/388,064, filed Jul. 29, 2021, Rotating Marker and Adapter for Image-Guided Surgery.
U.S. Appl. No. 18/291,731, filed Jan. 24, 2024, Rotating Marker and Adapter for Image-Guided Surgery.
U.S. Appl. No. 18/365,844, filed Aug. 4, 2023, Augmented-Reality Surgical System Using Depth Sensing.
U.S. Appl. No. 18/683,676, filed Feb. 14, 2024, Stereoscopic Display and Digital Loupe for Augmented-Reality Near-Eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-Guided Surgery.
U.S. Appl. No. 18/693,338, filed Mar. 19, 2024, Surgical Planning and Display.
U.S. Appl. No. 18/365,566, filed Aug. 4, 2023, Systems for Medical Image Visualization.
U.S. Appl. No. 18/399,253, filed Dec. 28, 2023, Methods for Medical Image Visualization.
U.S. Appl. No. 18/398,837, U.S. Pat. No. 12,044,858, filed Dec. 28, 2023, Jul. 23, 2024, Adjustable Augmented Reality Eyewear for Image-Guided Medical Intervention.
U.S. Appl. No. 18/399,433, U.S. Pat. No. 12,044,856, filed Dec. 28, 2023, Jul. 23, 2024, Configurable Augmented Reality Eyewear for Image-Guided Medical Intervention.
U.S. Appl. No. 18/772,578, filed Jul. 15, 2024, Augmented Reality Eyewear for Image-Guided Medical Intervention.
U.S. Appl. No. 35/508,942, U.S. Pat. No. 930,162, filed Feb. 13, 2020, Sep. 7, 2021, Medical Headset.
Augmedics Ltd., 510k Clearance Summary for Augmedics' xvision Spine system, dated Dec. 20, 2019 in 11 pages.
Medtronic Navigation, Inc., StealthStation™ S8 System Manual in 82 pages, Revision 2, Copyright 2018.
Novarad Healthcare IT and Imaging, OpenSight English: See 3D Medical Images Using Augmented Reality, dated Mar. 9, 2018, accessed via YouTube on Mar. 11, 2025 at https://www.youtube.com/watch?v=M3yY_b8jT54.

\* cited by examiner

AUGMENTED-REALITY SURGICAL SYSTEM USING DEPTH SENSING

CROSS-REFERENCE TO RELATED APPLICATIONS

This application is a continuation of International PCT Application PCT/IB2022/057733, filed Aug. 18, 2022, which claims the benefit of: U.S. Provisional Patent Application 63/236,241, filed Aug. 24, 2021; U.S. Provisional Patent Application 63/281,677, filed Nov. 21, 2021; U.S. Provisional Patent Application No. 63/234,272, filed Aug. 18, 2021; and U.S. Provisional Patent Application No. 63/236,244, filed Aug. 24, 2021. The entire content of each of these related applications is incorporated herein by reference.

FIELD

The present disclosure relates generally to image-guided surgery or intervention, and specifically to systems and methods for use of augmented reality in image-guided surgery or intervention and/or to systems and methods for use in surgical computer-assisted navigation.

BACKGROUND

Near-eye display devices and systems can be used in augmented reality systems, for example, for performing image-guided surgery. In this way, a computer-generated image may be presented to a healthcare professional who is performing the procedure such that the image is aligned with an anatomical portion of a patient who is undergoing the procedure. Applicant's own work has demonstrated an image of a tool that is used to perform the procedure can also be incorporated into the image that is presented on the head-mounted display. For example, Applicant's prior systems for image-guided surgery have been effective in tracking the positions of the patient's body and the tool (see, for example, U.S. Pat. Nos. 9,928,629, 10,835,296, 10,939,977, PCT International Publication WO 2019/211741, and U.S. Patent Application publication 2020/0163723.) The disclosures of all these patents and publications are incorporated herein by reference.

SUMMARY

Embodiments of the present disclosure provide improved systems, methods, and software for image-guided surgery. Some embodiments of the systems improve the accuracy of the augmented-reality images that are presented on the display and broaden the capabilities of the augmented reality system by employing depth sensing.

In some embodiments, a system for image-guided surgery comprises a head-mounted unit, comprising a see-through augmented-reality display and a depth sensor, which is configured to generate depth data with respect to a region of interest (ROI) of a body of a patient that is viewed through the display by a user wearing the head-mounted unit; and a processor, which is configured to receive a three-dimensional (3D) tomographic image of the body of the patient, to compute a depth map of the ROI based on the depth data generated by the depth sensor, to compute a transformation over the ROI so as to register the tomographic image with the depth map, and to apply the transformation in presenting a part of the tomographic image on the display in registration with the ROI viewed through the display.

In some embodiments, the ROI comprises a bone of the body to which an anchoring device is fastened, and wherein the processor is further configured to identify a location of the anchoring device in the depth map, to update the depth map in the course of a surgery, to detect a change in the location of the anchoring device in the updated depth map, and to take a corrective action responsively to the change.

In some embodiments, the corrective action comprises modifying a presentation on the display responsively to the change in the location of the anchoring device.

In some embodiments, the depth map includes a spine of the patient, which is exposed in a surgical procedure, and wherein the processor is configured to compute the transformation by registering the spine in the depth map with the spine appearing in the tomographic image.

In some embodiments, the processor is configured to process the depth data so as to detect a position of a marker that is fixed to the body of the patient, to recognize a location of the head-mounted unit relative to the body based on the detected position, and to position the image presented on the display responsively to the recognized location.

In some embodiments, the processor is configured to process the depth data so as to identify a change in an anatomical structure in the body of the patient during a surgical procedure, and to modify the image presented on the display responsively to the identified change.

In some embodiments, the processor is configured to process the depth data so as to identify an implant inserted into the body of the patient during a surgical procedure, and to modify the image presented on the display responsively to the identified implant.

In some embodiments, the tomographic image comprises a CT scan of the patient, which was performed with an array of radiopaque fiducial markers fixed to the body of the patient, and wherein the processor is configured to identify respective 3D coordinates of the fiducial markers in the depth map and to register the CT scan with the ROI viewed through the display by matching the fiducial markers in the CT to the respective 3D coordinates.

In some embodiments, a system for image-guided surgery comprises a head-mounted unit, comprising: a see-through augmented-reality display; and a depth sensor, which is configured to generate depth data with respect to a region of interest (ROI) on a body of a patient that is viewed through the display by a user wearing the head-mounted unit and with respect to a surgical tool when the tool is placed within a field of view of the depth sensor, wherein the tool comprises a shaft and a marker containing a predefined pattern disposed on the tool in a fixed spatial relation to the shaft; and a processor, which is configured to: process the depth data so as to identify a shape of the tool and to compute, responsively to the shape, a spatial transformation between a position of the marker and a location and orientation of the shaft; track the position of the marker as the user manipulates the shaft of the tool within the body, and using the tracked position and the spatial transformation, generate an image of the tool, including the shaft, on the display in registration with the ROI viewed through the display.

In some embodiments, further comprising a tracking sensor, which is disposed on the head-mounted unit in a known spatial relation to the depth sensor and is configured to detect the position of the marker.

In some embodiments, the shaft has a curved shape, and wherein the processor is configured to process the depth data so as to reconstruct a three-dimensional (3D) model of the curved shape, and to generate the image of the tool based on the 3D model.

In some embodiments, the processor is configured to process the depth data so as detect a change in a shape of the tool and to update the image of the tool on the display responsively to the change in the shape.

In some embodiments, the depth sensor is further configured to generate the depth data with respect to a further marker that is attached to the body of the patient, and wherein the processor is configured to apply the depth data in calculating a position of the tool relative to the body.

In some embodiments, the depth sensor is configured to generate further depth data with respect to a hand of a user of the head-mounted unit, and wherein the processor is configured to process the further depth data so as to detect a gesture made by the hand, and to control a function of the system responsively to the detected gesture.

In some embodiments, a system for image-guided surgery, comprises a head-mounted unit, comprising a see-through augmented-reality display and a depth sensor, which is configured to generate depth data with respect to a region of interest (ROI) on a body of a patient that is viewed through the display by a user wearing the head-mounted unit and with respect to a surgical implant when the implant is placed within a field of view of the depth sensor, wherein the implant is configured to be mounted on a shaft of a surgical tool and inserted, using the tool, into the body; and a processor, which is configured to process the depth data so as to identify a shape of the implant and to compute, responsively to the shape, a spatial transformation between a position of a marker disposed on the tool and a location and orientation of the implant, to track the position of the marker as the user manipulates the shaft of the tool within the body, and using the tracked position, the spatial transformation, and the identified shape, to generate on the display an image of the implant within the body in registration with the ROI viewed through the display, wherein the marker contains a predefined pattern and is disposed in a fixed spatial relation to the shaft.

In some embodiments, the system further comprising a tracking sensor, which is disposed on the head-mounted unit in a known spatial relation to the depth sensor and is configured to detect the position of the marker.

In some embodiments, the shaft has a curved shape, and wherein the processor is configured to process the depth data so as to reconstruct a three-dimensional (3D) model of the curved shape, and to generate the image of the implant based on the 3D model.

In some embodiments, the processor is configured to process the depth data so as detect a change in a shape of the tool and to update the spatial transformation responsively to the change in the shape.

In some embodiments, a system for image-guided surgery, comprises a head-mounted unit, comprising a see-through augmented-reality display and a depth sensor, which is configured to generate depth data with respect to a region of interest (ROI) on a body of a patient, including a bone inside the body, that is viewed through the display by a user wearing the head-mounted unit; and a processor, which is configured to process the depth data generated by the depth sensor so as to identify a first three-dimensional (3D) shape of the bone prior to a surgical procedure on the bone and a second 3D shape of the bone following the surgical procedure, and to generate, based on the first and second 3D shapes, an image showing a part of the bone that was removed in the surgical procedure.

In some embodiments, a method for image-guided surgery comprises using a head-mounted unit that includes a see-through augmented-reality display and a depth sensor, generating depth data with respect to a region of interest (ROI) of a body of a patient that is viewed through the display by a user wearing the head-mounted unit; receiving a three-dimensional (3D) tomographic image of the body of the patient; computing a depth map of the ROI based on the depth data generated by the depth sensor; computing a transformation over the ROI so as to register the tomographic image with the depth map; and applying the transformation in presenting a part of the tomographic image on the display in registration with the ROI viewed through the display.

In some embodiments, the ROI comprises a bone of the body to which an anchoring device is fastened, and wherein the method comprises: identifying an initial location of the anchoring device in the depth map; updating the depth map in the course of a surgery; detecting a change in the location of the anchoring device in the updated depth map; and taking a corrective action responsively to the change.

In some embodiments, taking the corrective action comprises modifying a presentation on the display responsively to the change in the location of the anchoring device.

In some embodiments, the depth map includes a spine of the patient, which is exposed in a surgical procedure, and wherein computing the transformation comprises registering the spine in the depth map with the spine appearing in the tomographic image.

In some embodiments, the method further comprises processing the depth data so as to detect a position of a marker that is fixed to the body of the patient; recognizing a location of the head-mounted unit relative to the body based on the detected position; and positioning the image presented on the display responsively to the recognized location.

In some embodiments, the method further comprises processing the depth data so as to identify a change in an anatomical structure in the body of the patient during a surgical procedure; and modifying the image presented on the display responsively to the identified change.

In some embodiments, the method further comprises processing the depth data so as to identify an implant inserted into the body of the patient during a surgical procedure; and modifying the image presented on the display responsively to the identified implant.

In some embodiments, the tomographic image comprises a CT scan of the patient, which was performed with an array of radiopaque fiducial markers fixed to the body of the patient, and wherein computing the transformation comprises identifying respective 3D coordinates of the fiducial markers in the depth map, and registering the CT scan with the ROI viewed through the display by matching the fiducial markers in the CT to the respective 3D coordinates.

In some embodiments, a method for image-guided surgery comprises using a head-mounted unit that includes a see-through augmented-reality display and a depth sensor, generating depth data with respect to a region of interest (ROI) on a body of a patient that is viewed through the display by a user wearing the head-mounted unit and with respect to a surgical tool when the tool is placed within a field of view of the depth sensor, wherein the tool comprises a shaft and a marker containing a predefined pattern disposed on the tool in a fixed spatial relation to the shaft; processing the depth data so as to identify a shape of the tool and to compute, responsively to the shape, a spatial transformation between a position of the marker and a location and orientation of the shaft; tracking the position of the marker as the user manipulates the shaft of the tool within the body; and using the tracked position and the spatial transformation, generating an image of the tool, including the shaft, on the display in registration with the ROI viewed through the display.

In some embodiments, the tracking the position comprises detecting the position of the marker using a tracking sensor disposed on the head-mounted unit in a known spatial relation to the depth sensor.

In some embodiments, the shaft has a curved shape, and wherein processing the depth data comprises reconstructing a three-dimensional (3D) model of the curved shape, wherein the image of the tool is generated based on the 3D model.

In some embodiments, processing the depth data comprises detecting a change in a shape of the tool, and wherein generating the image comprises updating the image of the tool on the display responsively to the change in the shape.

In some embodiments, generating the depth data comprises capturing further depth data with respect to a further marker that is attached to the body of the patient, and wherein processing the depth data comprises applying the further depth data in calculating a position of the tool relative to the body.

In some embodiments, generating the depth data comprises capturing further depth data with respect to a hand of a user of the head-mounted unit, and wherein the method comprises processing the further depth data so as to detect a gesture made by the hand, and controlling a function of the head-mounted unit responsively to the detected gesture.

In some embodiments, a method for image-guided surgery comprises using a head-mounted unit that includes a see-through augmented-reality display and a depth sensor, generating depth data with respect to a region of interest (ROI) on a body of a patient that is viewed through the display by a user wearing the head-mounted unit and with respect to a surgical implant when the implant is placed within a field of view of the depth sensor, wherein the implant is mounted on a shaft of a surgical tool and inserted, using the tool, into the body; processing the depth data so as to identify a shape of the implant; computing, responsively to the shape, a spatial transformation between a position of a marker disposed on the tool and a location and orientation of the implant, wherein the marker contains a predefined pattern and is disposed in a fixed spatial relation to the shaft; tracking the position of the marker as the user manipulates the shaft of the tool within the body; and using the tracked position, the spatial transformation, and the identified shape, generating on the display an image of the implant within the body in registration with the ROI viewed through the display.

In some embodiments, the method further comprises detecting the position of the marker using a tracking sensor, which is disposed on the head-mounted unit in a known spatial relation to the depth sensor.

In some embodiments, the shaft has a curved shape, and wherein processing the depth data comprises reconstructing a three-dimensional (3D) model of the curved shape, wherein the image of the implant is generated based on the 3D model.

In some embodiments, processing the depth data comprises detecting a change in a shape of the tool, and updating the spatial transformation responsively to the change in the shape.

In some embodiments, a method for image-guided surgery, comprises using a head-mounted unit that includes a see-through augmented-reality display and a depth sensor, generating depth data with respect to a region of interest (ROI) on a body of a patient, including a bone inside the body, that is viewed through the display by a user wearing the head-mounted unit; processing the depth data generated by the depth sensor so as to identify a first three-dimensional (3D) shape of the bone prior to a surgical procedure on the bone and a second 3D shape of the bone following the surgical procedure; and generating, based on the first and second 3D shapes, an image showing a part of the bone that was removed in the surgical procedure.

In some embodiments, the surgical procedure involves a bone cut.

In some embodiments, a head-mounted system for image-guided surgery comprises a see-through augmented-reality display disposed so as to be viewable by a user over a region of interest (ROI) of a body of a patient; a depth sensor configured to generate depth data with respect to the ROI; and a processor and a memory for storing instructions that, when executed by the processor cause the system to: receive a three-dimensional (3D) tomographic image of the body of the patient; determine a depth map of the ROI based at least in part on the depth data; determine a transformation over the ROI so as to register the 3D tomographic image with the depth map; and display at least a part of the 3D tomographic image on the see-through augmented-reality display in registration with the ROI based at least in part on the transformation.

In some embodiments, a method for image-guided surgery comprises a see-through augmented-reality display disposed so as to be viewable by a user over a region of interest (ROI) of a body of a patient; a depth sensor configured to generate depth data with respect to the ROI; and a processor and a memory for storing instructions that, when executed by the processor cause the system to: receive a three-dimensional (3D) tomographic image of the body of the patient; determine a depth map of the ROI based at least in part on the depth data; determine a transformation over the ROI so as to register the 3D tomographic image with the depth map; and display at least a part of the 3D tomographic image on the see-through augmented-reality display in registration with the ROI based at least in part on the transformation.

For purposes of summarizing the disclosure, certain aspects, advantages, and novel features are discussed herein. It is to be understood that not necessarily all such aspects, advantages, or features will be embodied in any particular embodiment of the disclosure, and an artisan would recognize from the disclosure herein a myriad of combinations of such aspects, advantages, or features.

The present invention will be more fully understood from the following detailed description of the embodiments thereof, taken together with the drawings in which:

BRIEF DESCRIPTION OF THE DRAWINGS

Non-limiting features of some embodiments of the invention are set forth with particularity in the claims that follow. The following drawings are for illustrative purposes only and show non-limiting embodiments. Features from different figures may be combined in several embodiments.

DETAILED DESCRIPTION

Overview

Embodiments of the present disclosure that are described herein provide systems, methods and software for image-guided surgery or other intervention, computer assisted navigation and/or stereotactic surgery or other intervention that, inter alia, use depth sensing to enhance the capabilities of an augmented-reality display and system. In some embodiments, a head-mounted unit comprises both a see-through augmented-reality display and a depth sensor. In some embodiments, the depth sensor generates depth data with respect to a region of interest (ROI) on a body of a patient that is viewed through the display by a user wearing the head-mounted unit. In some embodiments, the system applies the depth data in generating one or more depth maps of the body. Additionally or alternatively, the depth sensor may be applied in generating depth data with respect to implements such as clamps, tools and implants that can be inserted into the body. In some embodiments, using the depth data, the system is able to improve the accuracy of the augmented-reality images that are presented on the display and broaden the capabilities of the augmented-reality system.

In some embodiments, the term "depth sensor" refers to one or more optical components that are configured to capture a depth map of a scene. For example, in some embodiments, the depth sensor can be a pattern projector and a camera for purposes of structured-light depth mapping. For example, in some embodiments, the depth sensor can be a pair of cameras configured for stereoscopic depth mapping. For example, in some embodiments, the depth sensor can be a beam projector and a detector (or an array of detectors) configured for time-of-flight measurement. Of course the term "depth sensor" as used herein is not limited to the listed examples and can other structure.

System Description

Figure 1:
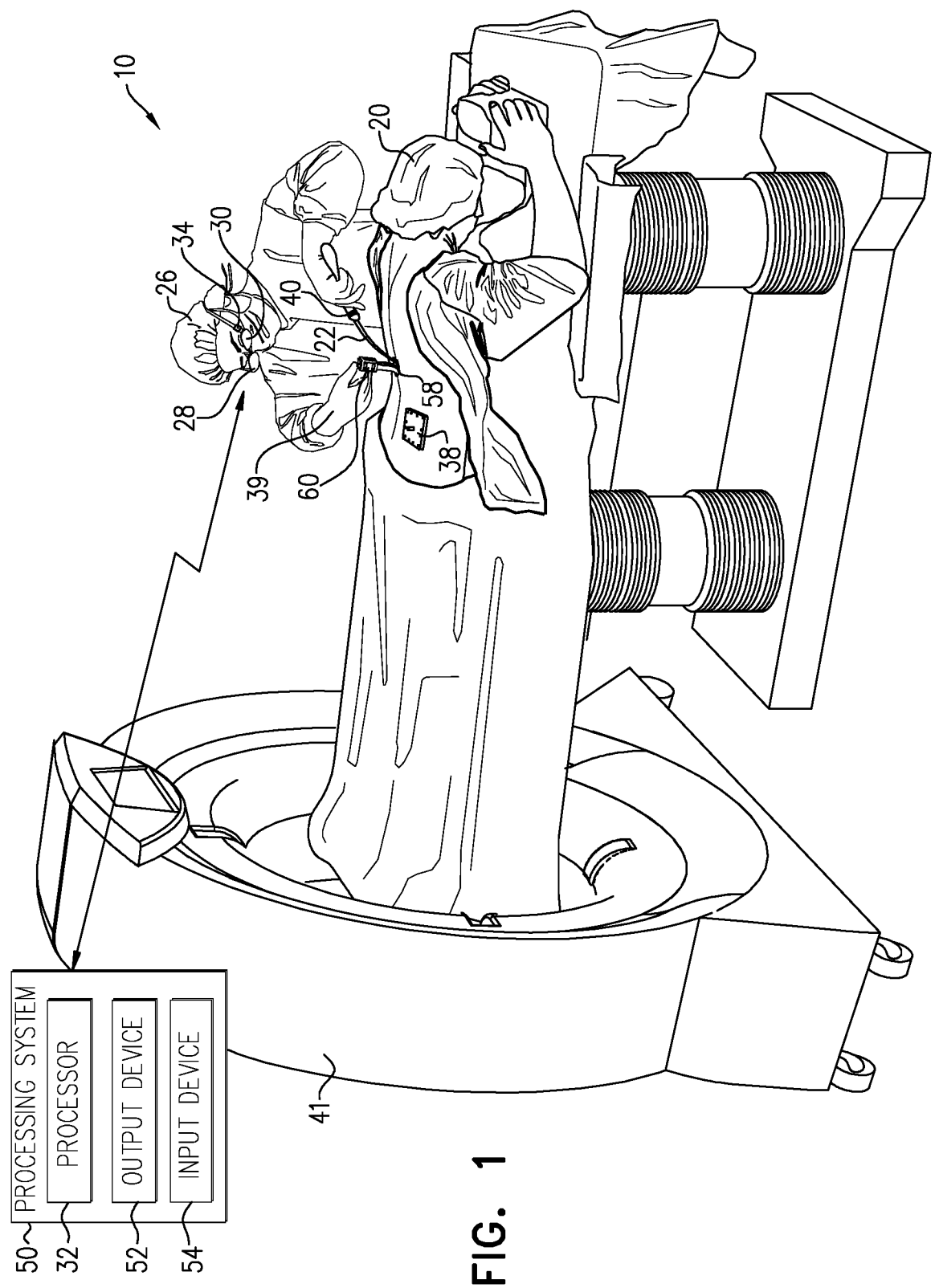
FIG. 1 is a schematic pictorial illustration showing a system for image-guided surgery, in accordance with an embodiment of the disclosure.
Figure 2A:
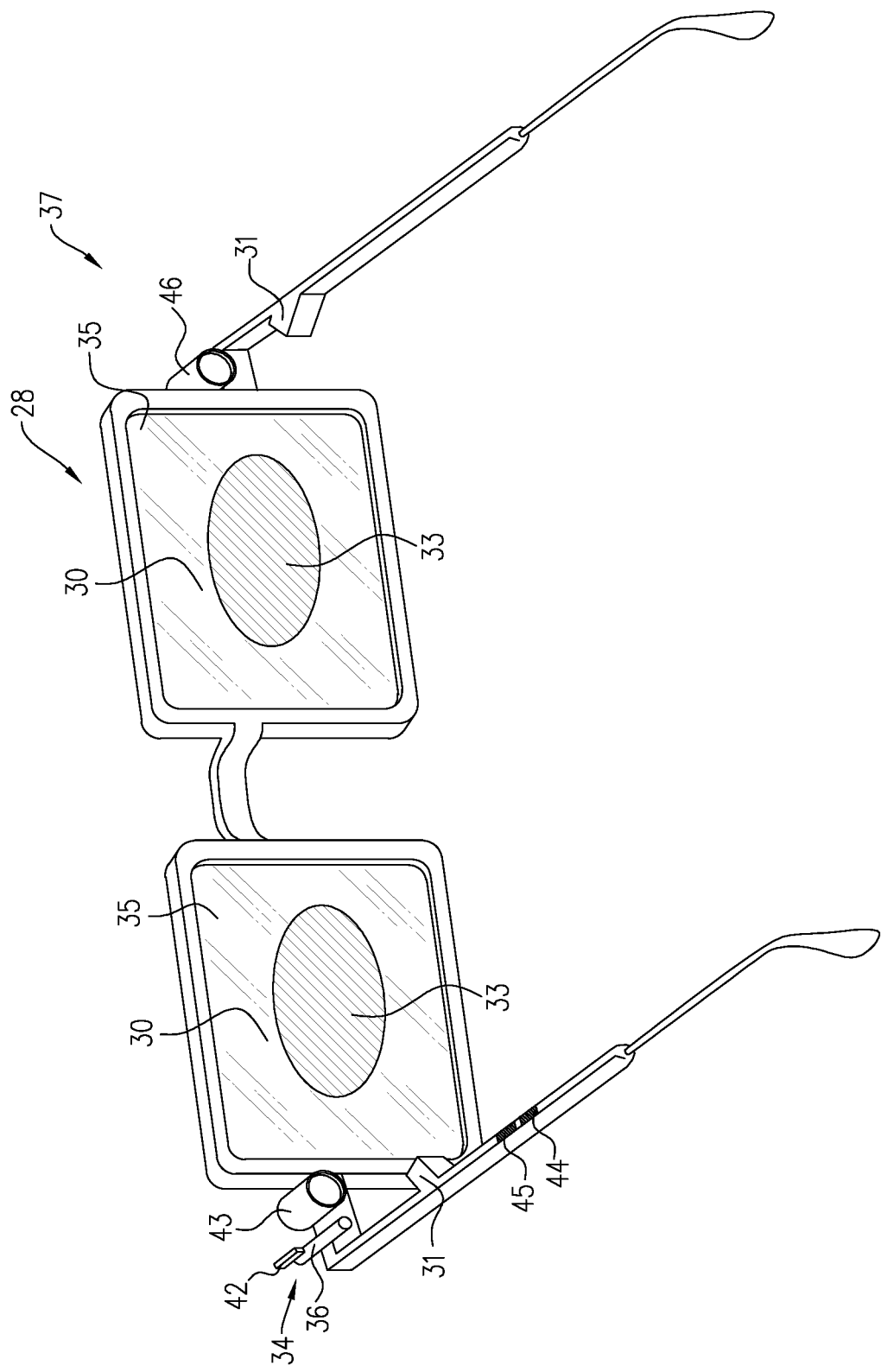
FIG. 2A is a schematic pictorial illustration showing details of a near-eye unit that is used for image-guided surgery, in accordance with an embodiment of the disclosure.

Reference is now made to FIGS. 1 and 2A, which schematically illustrate an exemplary system 10 for image-guided surgery, in accordance with some embodiments of the disclosure. For example, FIG. 1 is a pictorial illustration of the system 10 as a whole, while FIG. 2A is a pictorial illustration of a near-eye unit that is used in the system 10. The near eye unit illustrated in FIGS. 1 and 2A is configured as a head-mounted unit 28. In some embodiments, the near-eye unit can be configured as the head-mounted unit 28 shown in FIG. 8 and as a head-mounted AR display (HMD) unit 70, 100 and described hereinbelow. In FIG. 1, the system 10 is applied in a medical procedure on a patient 20 using image-guided surgery. In this procedure, a tool 22 is inserted via an incision in the patient's back in order to perform a surgical intervention. Alternatively, the system 10 and the techniques described herein may be used, mutatis mutandis, in other surgical procedures.

Methods for optical depth mapping can generate a three-dimensional (3D) profile of the surface of a scene by processing optical radiation reflected from the scene. In the context of the present description and in the claims, the terms depth map, 3D profile, and 3D image are used interchangeably to refer to an electronic image in which the pixels contain values of depth or distance from a reference point, instead of or in addition to values of optical intensity.

In some embodiments, depth mapping systems can use structured light techniques in which a known pattern of illumination is projected onto the scene. Depth can be calculated based on the deformation of the pattern in an image of the scene. In some embodiments, depth mapping systems use stereoscopic techniques, in which the parallax shift between two images captured at different locations is used to measure depth. In some embodiments, depth mapping systems can sense the times of flight of photons to and from points in the scene in order to measure the depth coordinates. In some embodiments, depth mapping systems control illumination and/or focus and can use various sorts of image processing techniques.

In the embodiment illustrated in FIG. 1, a user of the system 10, such as a healthcare professional 26 (for example, a surgeon performing the procedure), wears the head-mounted unit 28. In some embodiments, the head-mounted unit 28 includes one or more see-through displays 30, for example as described in the above-mentioned U.S. Pat. No. 9,928,629 or in the other patents and applications cited above.

In some embodiments, the one or more see-through displays 30 include an optical combiner. In some embodiments, the optical combiner is controlled by one or more processors 32. In some embodiments, the one or more processors 32 is disposed in a central processing system 50. In some embodiments, the one or more processors 32 is disposed in the head-mounted unit 28. In some embodiments, the one or more processors 32 are disposed in both the central processing system 50 and the head-mounted unit 28 and can share processing tasks and/or allocate processing tasks between the one or more processors 32.

In some embodiments, the one or more see-through displays 30 display an augmented-reality image to the healthcare professional 26. In some embodiments, the augmented reality image viewable through the one or more see-through displays 30 is a combination of objects visible in the real world with the computer-generated image. In some embodiments, each of the one or more see-through displays 30 comprises a first portion 33 and a second portion 35. In some embodiments, the one or more see-through displays 30 display the augmented-reality image such that the computer-generated image is projected onto the first portion 33 in alignment with the anatomy of the body of the patient 20 that is visible to the healthcare professional 26 through the second portion 35.

In some embodiments, the computer-generated image includes a virtual image of one or more tools 22. In some embodiments, the system 10 combines at least a portion of the virtual image of the one or more tools 22 into the computer-generated image. For example, some or all of the tool 22 may not be visible to the healthcare professional 26 because, for example, a portion of the tool 22 is hidden by the patient's anatomy (e.g., a distal end of the tool 22). In some embodiments, the system 10 can display the virtual image of at least the hidden portion of the tool 22 as part of the computer-generated image displayed in the first portion 33. In this way, the virtual image of the hidden portion of the tool 22 is displayed on the patient's anatomy. In some embodiments, the portion of the tool 22 hidden by the patient's anatomy increase and/or decreases over time or during the procedure. In some embodiments, the system 10 increase and/or decreases the portion of the tool 22 included in the computer-generated image based on the changes in the portion of the tool 22 hidden by the patient's anatomy over time.

Some embodiments of the system 10 comprise an anchoring device (e.g., bone marker 60) for indicating the body of the patient 20. For example, in image-guided surgery and other surgeries that utilize the system 10, the bone marker 60 can be used as a fiducial marker. In some embodiments, the bone marker 60 can be coupled with the fiducial marker. In system 10, for example, the anchoring device is configured as the bone marker 60 (e.g., anchoring device coupled with a marker that is used to register an ROI of the body of the patient 20). In some embodiments, the anchoring device is coupled with a tracking system, with a preoperative or intraoperative CT scan of the ROI. During the procedure, in some embodiments, the tracking system (for example an IR tracking system) tracks the marker mounted on the anchoring device and the tool 22 mounted with a tool marker 40. Following that, the display of the CT image data, including, for example, a model generated based on such data, on the near-eye display may be aligned with the surgeon's actual view of the ROI based on this registration. In addition, a virtual image of the tool 22 may be displayed on the CT model based on the tracking data and the registration. The user may then navigate the tool 22 based on the virtual display of the tool 22 with respect to the patient image data, and optionally, while it is aligned with the user view of the patient or ROI.

According to some aspects, the image presented on the one or more see-through displays 30 is aligned with the body of the patient 20. According to some aspects, misalignment of the image presented on the one or more see-through displays 30 with the body of the patient 20 may be allowed. In some embodiments, the misalignment may be 0-1 mm, 1-2 mm, 2-3 mm, 3-4 mm, 4-5 mm, 5-6 mm, and overlapping ranges therein. According to some aspects, the misalignment may typically not be more than about 5 mm. In order to account for such a limit on the misalignment of the patient's anatomy with the presented images, the position of the patient's body, or a portion thereof, with respect to the head-mounted unit 28 can be tracked. For example, in some embodiments, a patient marker 38 and/or the bone marker 60 attached to an anchoring implement or device such as a clamp 58 or pin, for example, may be used for this purpose, as described further hereinbelow.

When an image of the tool 22 is incorporated into the computer-generated image that is displayed on the head-mounted unit 28 or the HMD unit 70, the position of the tool 22 with respect to the patient's anatomy should be accurately reflected. For this purpose, the position of the tool 22 or a portion thereof, such as the tool marker 40, is tracked by the system 10. In some embodiments, the system 10 determines the location of the tool 22 with respect to the patient's body such that errors in the determined location of the tool 22 with respect to the patient's body are reduced. For example, in certain embodiments, the errors may be 0-1 mm, 1-2 mm, 2-3 mm, 3-4 mm, 4-5 mm, and overlapping ranges therein.

In some embodiments, the head-mounted unit 28 includes a tracking sensor 34 to facilitate determination of the location and orientation of the head-mounted unit 28 with respect to the patient's body and/or with respect to the tool 22. In some embodiments, tracking sensor 34 can also be used in finding the position and orientation of the tool 22 and the clamp 58 with respect to the patient's body. In some embodiments, the tracking sensor 34 comprises an image-capturing device 36, such as a camera, which captures images of the patient marker 38, the bone marker 60, and/or the tool marker 40. For some applications, an inertial-measurement unit 44 is also disposed on the head-mounted unit 28 to sense movement of the user's head.

In some embodiments, the tracking sensor 34 includes a light source 42. In some embodiments, the light source 42 is mounted on the head-mounted unit 28. In some embodiments, the light source 42 irradiates the field of view of the image-capturing device 36 such that light reflects from the patient marker 38, the bone marker 60, and/or the tool marker 40 toward the image-capturing device 36. In some embodiments, the image-capturing device 36 comprises a monochrome camera with a filter that passes only light in the wavelength band of light source 42. For example, the light source 42 may be an infrared light source, and the camera may include a corresponding infrared filter. In some embodiments, the patient marker 38, the bone marker 60, and/or the tool marker 40 comprise patterns that enable a processor to compute their respective positions, i.e., their locations and their angular orientations, based on the appearance of the patterns in images captured by the image-capturing device 36. Suitable designs of these markers and methods for computing their positions and orientations are described in the patents and patent applications incorporated herein and cited above.

In addition to or instead of the tracking sensor 34, the head-mounted unit 28 can include a depth sensor 37. In the embodiment shown in FIG. 2A, the depth sensor 37 comprises a light source 46 and a camera 43. In some embodiments, the light source 46 projects a pattern of structured light onto the region of interest (ROI) that is viewed through the one or more displays 30 by a user, such as professional 26, who is wearing the head-mounted unit 28. The camera 43 can capture an image of the pattern on the ROI and output the resulting depth data to the processor 32 and/or processor 45. The depth data may comprise, for example, either raw image data or disparity values indicating the distortion of the pattern due to the varying depth of the ROI. In some embodiments, the processor 32 computes a depth map of the ROI based on the depth data generated by the camera 43.

In some embodiments, the camera 43 also captures and outputs image data with respect to the markers in system 10, such as patient marker 38, bone marker 60, and/or tool marker 40. In this case, the camera 43 may also serve as a part of tracking sensor 34, and a separate image-capturing device 36 may not be needed. For example, the processor 32 may identify patient marker 38, bone marker 60, and/or tool marker 40 in the images captured by camera 43. The processor 32 may also find the 3D coordinates of the markers in the depth map of the ROI. Based on these 3D coordinates, the processor 32 is able to calculate the relative positions of the markers, for example in finding the position of the tool 22 relative to the body of the patient 20, and can use this information in generating and updating the images presented on head-mounted unit 28.

In some embodiments, the depth sensor 37 may apply other depth mapping technologies in generating the depth data. For example, the light source 46 may output pulsed or time-modulated light, and the camera 43 may be modified or replaced by a time-sensitive detector or detector array to measure the time of flight of the light to and from points in the ROI. As another option, the light source 46 may be replaced by another camera, and the processor 32 may compare the resulting images to those captured by the camera 43 in order to perform stereoscopic depth mapping. These and all other suitable alternative depth mapping technologies are considered to be within the scope of the present disclosure.

In the pictured embodiment, system 10 also includes a tomographic imaging device, such as an intraoperative computerized tomography (CT) scanner 41. Alternatively or additionally, processing system 50 may access or otherwise receive tomographic data from other sources; and the CT scanner itself is not an essential part of the present system. In some embodiments, regardless of the source of the tomographic data, the processor 32 can computes a transformation over the ROI so as to register the tomographic images with the depth maps that it computes on the basis of the depth data provided by depth sensor 37. The processor 32 can then apply this transformation in presenting a part of the tomographic image on the one or more displays 30 in registration with the ROI viewed through the one or more displays 30. This functionality is described further hereinbelow with reference to FIG. 4A.

In some embodiments, in order to generate and present an augmented reality image on the one or more displays 30, the processor 32 computes the location and orientation of the head-mounted unit 28 with respect to a portion of the body of patient 20, such as the patient's back. In some embodiments, the processor 32 also computes the location and orientation of the tool 22 with respect to the patient's body. In some embodiments, the processor 45, which can be integrated within the head-mounted unit 28, may perform these functions. Alternatively or additionally, the processor 32, which is disposed externally to the head-mounted unit 28 and can be in wireless communication with the head-mounted unit 28, may be used to perform these functions. The processor 32 can be part of the processing system 50, which can include an output device 52, for example a display, such as a monitor, for outputting information to an operator of the system, and/or an input device 54, such as a pointing device, a keyboard, or a mouse, to allow the operator to input data into the system.

Alternatively or additionally, users of the system 10 may input instructions to the processing system 50 using a gesture-based interface. For this purpose, for example, the depth sensor 37 may sense movements of a hand 39 of the healthcare professional 26. Different movements of the professional's hand and fingers may be used to invoke specific functions of the one or more displays 30 and of the system 10.

In general, in the context of the present description, when a computer processor is described as performing certain steps, these steps may be performed by external computer processor 32 and/or computer processor 45 that is integrated within the head-mounted unit. The processor or processors carry out the described functionality under the control of suitable software, which may be downloaded to system 10 in electronic form, for example over a network, and/or stored on tangible, non-transitory computer-readable media, such as electronic, magnetic, or optical memory.

Figure 2B:
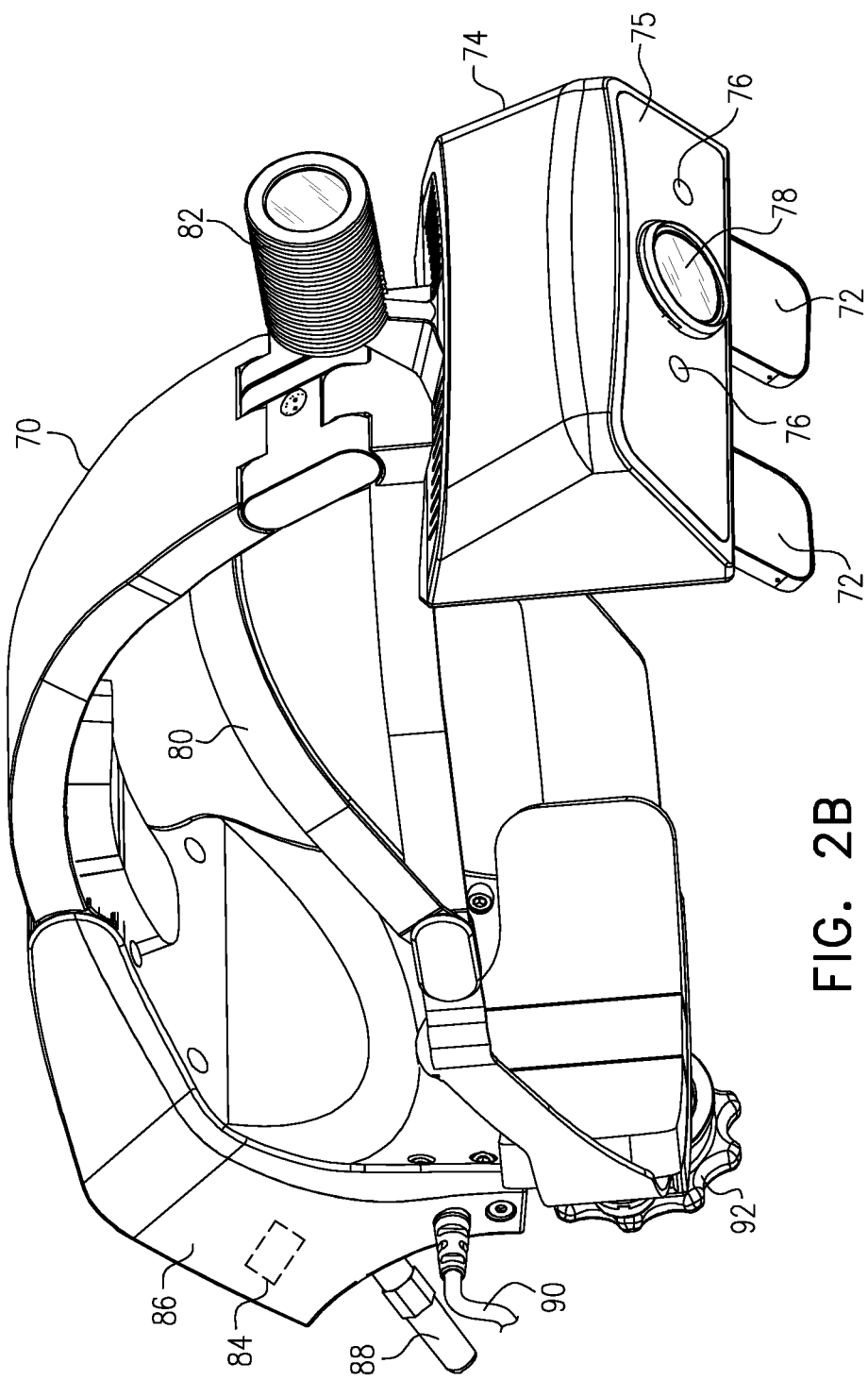
FIG. 2B is a schematic pictorial illustration showing details of a head-mounted unit that is used for image-guided surgery, in accordance with another embodiment of the disclosure.

FIG. 2B is a schematic pictorial illustration showing details of a head-mounted AR display (HMD) unit 70, according to another embodiment of the disclosure. HMD unit 70 may be worn by the healthcare professional 26, and may be used in place of the head-mounted unit 28 (FIG. 1). HMD unit 70 comprises an optics housing 74 which incorporates a camera 78, and in the specific embodiment shown, an infrared camera. In some embodiments, the housing 74 comprises an infrared-transparent window 75, and within the housing, i.e., behind the window, are mounted one or more, for example two, infrared projectors 76. One of the infrared projectors and the camera may be used, for example, in implementing a pattern-based depth sensor.

In some embodiments, mounted on housing 74 are a pair of augmented reality displays 72, which allow professional 26 to view entities, such as part or all of patient 20, through the displays, and which are also configured to present to surgeon images or any other information. In some embodiments, the displays 72 present planning and guidance information, as described above.

In some embodiments, the HMD unit 70 includes a processor 84, mounted in a processor housing 86, which operates elements of the HMD unit. In some embodiments, an antenna 88, may be used for communication, for example with processor 32 (FIG. 1).

In some embodiments, a flashlight 82 may be mounted on the front of HMD unit 70. In some embodiments, the flashlight may project visible light onto objects so that professional is able to clearly see the objects through displays 72. In some embodiments, elements of the HMD unit 70 are powered by a battery (not shown in the figure), which supplies power to the elements via a battery cable input 90.

In some embodiments, the HMD unit 70 is held in place on the head of professional 26 by a head strap 80, and the professional may adjust the head strap by an adjustment knob 92.

In some embodiments, the HMD may comprise a visor, which includes an AR display positioned in front of each eye of the professional and controlled by the optical engine to project AR images into the pupil of the eye.

In some embodiments, the HMD may comprise a light source for tracking applications, comprising, for example, a pair of infrared (IR) LED projectors, configured to direct IR beams toward the body of patient 20. In some embodiments, the light source may comprise any other suitable type of one or more light sources, configured to direct any suitable wavelength or band of wavelengths of light. The HMD may also comprise one or more cameras, for example, a red/green/blue (RGB) camera having an IR-pass filter, or a monochrome camera configured to operate in the IR wavelengths. The one or more camera s may be configured to capture images including the markers in system 10 (FIG. 1).

In some embodiments, the HMD may also comprise one or more additional cameras, e.g., a pair of RGB cameras. In some embodiments, each RGB camera may be configured to produce high-resolution RGB (HR RGB) images of the patient's body, which can be presented on the AR displays. Because the RGB cameras are positioned at a known distance from one another, the processor can combine the images to produce a stereoscopic 3D image of the site being operated on.

In some embodiments, the HMD light source 46 (FIG. 2A) may comprises a structured light projector (SLP) which projects a pattern onto an area of the body of patient 20 on which professional 26 is operating. In some embodiments, light source 46 comprises a laser dot pattern projector, which is configured to apply to the area structured light comprising a large number (typically between hundreds and hundreds of thousands) of dots arranged in a suitable pattern. This pattern serves as an artificial texture for identifying positions on large anatomical structures lacking fine details of their own, such as the skin and surfaces of the vertebrae. In some embodiments, one or more cameras 43 capture images of the pattern, and a processor, such as processor 32 (FIG. 1), processes the images in order to produce a depth map of the area. In some embodiments, the depth map is calculated based on the local disparity of the images of the pattern relative to an undistorted reference pattern, together with the known offset between the light source and the camera.

In some embodiments, the projected pattern comprises a pseudorandom pattern of dots. In this case, clusters of dots can be uniquely identified and used for disparity measurements. In the present example, the disparity measurements may be used for calculating depth and for enhancing the precision of the 3D imaging of the area of the patient's body. In some embodiments, the wavelength of the pattern may be in the visible or the infrared range.

In some embodiments, the system 10 (FIG. 1) may comprise a structured light projector (not shown) mounted on a wall or on an arm of the operating room. In such embodiments, a calibration process between the structured light projector and one or more cameras on the head-mounted unit or elsewhere in the operating room may be performed to obtain the 3D map.

Figure 3A:
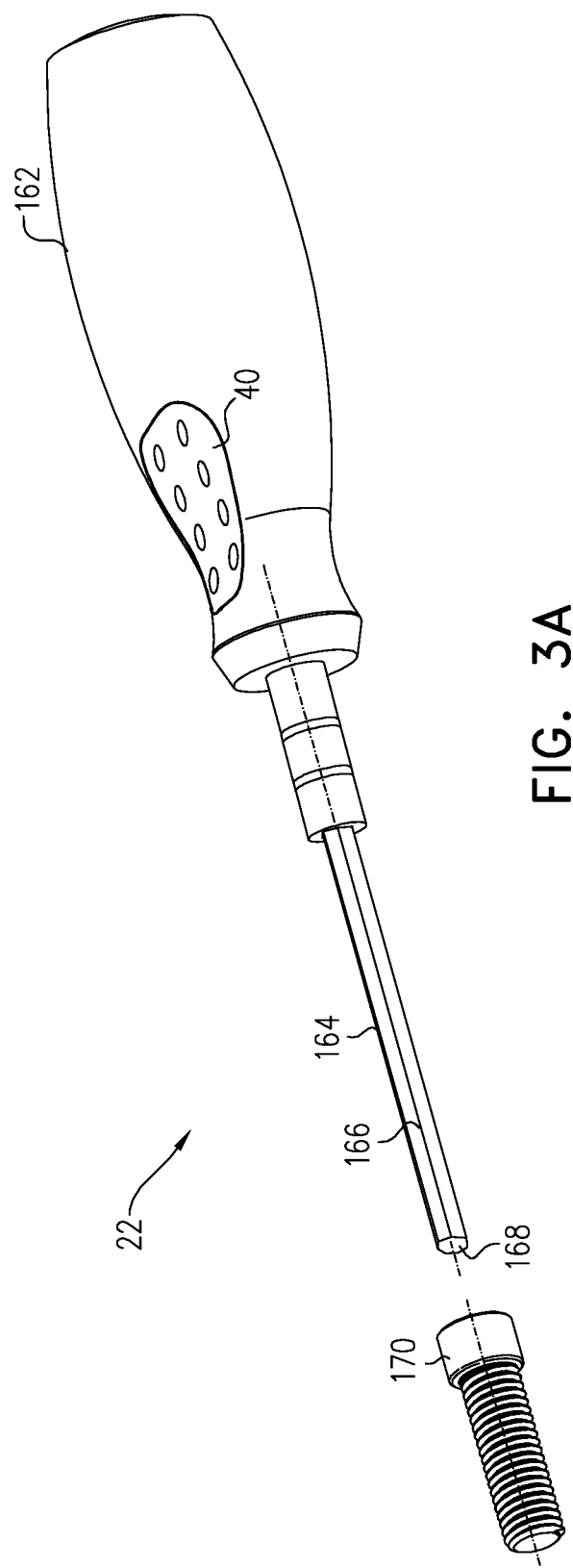
FIG. 3A is a schematic pictorial illustration showing details of a surgical tool, in accordance with an embodiment of the disclosure.

FIG. 3A is a schematic pictorial illustration showing details of the tool 22, in accordance with an embodiment of the disclosure. In some embodiments, the tool 22 comprises a handle 162 and a shaft 164. In some embodiments, the marker 40, containing a predefined pattern, is disposed on the handle 162 in a fixed spatial relation to shaft 164. Alternatively, marker 40 may protrude outward from tool 22 to ensure that it is visible to tracking sensor 34 and/or camera 43 (FIG. 2A). Additionally or alternatively, the depth sensor 37 generates depth data with respect to tool 22. Uses of the depth data in tracking and displaying images of tool 22 are described further hereinbelow with reference to FIG. 5.

In some embodiments, based on the image information provided by tracking sensor 34 and/or camera 43, processor 32 (or processor 45) is able to compute the position (location and orientation) of marker 40 and to track changes in the position of the marker during the surgical procedure. In some embodiments, using the computed position and the known spatial relation of marker 40 to shaft 164, processor 32 is thus able to find the orientation angle of a longitudinal axis 166 of shaft 164 and the location of a distal end 168 of the shaft, even when the shaft is inside the patient's body. On this basis, processor 32 generates an image of tool 22, including shaft 164, on displays 30 in registration with the ROI viewed through the displays.

In the example shown in FIG. 3A, tool 22 is used in inserting a surgical implant 170 into the body of patient 20. For the purpose of insertion, implant 170 is mounted on distal end 168 of shaft 164. In one embodiment, the depth sensor 37 captures depth data with respect to both tool 22 and implant 170. In some embodiments, the processor 32 uses the depth data in generating and displaying images of both the tool and the implant, as described further hereinbelow with reference to FIG. 6.

Figure 3B:
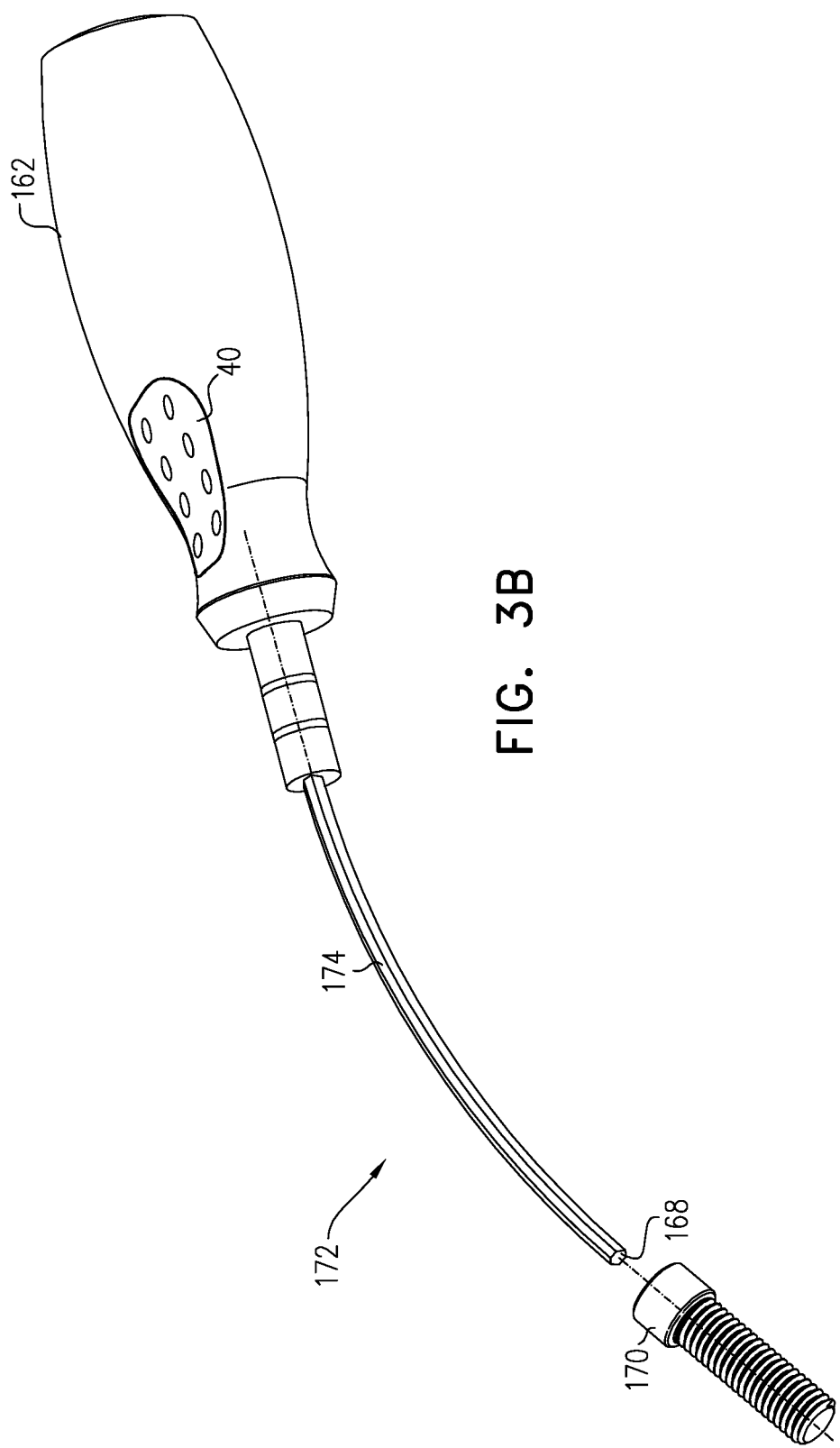
FIG. 3B is a schematic pictorial illustration showing details of a surgical tool, in accordance with another embodiment of the disclosure.

FIG. 3B is a schematic pictorial illustration showing details of tool 172, in accordance with an alternative embodiment of the disclosure. Tool 172 is similar to tool 22 and includes similar components, which are labeled with the same indicator numbers. In contrast to tool 22, however, tool 172 has a curved shaft 174. The curvature of shaft 174 may be fixed, or it may be malleable or otherwise bendable, so that the shape of the shaft may vary from one operation to another or even during a single operation.

To identify the actual shape of shaft 174, processor 32 receives and analyzes a depth map that includes tool 172. The depth map may be captured using any suitable mapping and/or imaging technique, such as the various techniques described above. In some embodiments, the processor 32 segments the depth map to identify the 3D shape of shaft 174 and thus reconstructs a 3D model of tool 172. Based on this 3D model, together with the location of tool marker 40, in some embodiments, the processor 32 is able to compute the location of distal end 168 of shaft 174 even when the distal end is hidden from sight inside the patient's body. In some embodiments, the processor 32 can use the depth data in generating and displaying images of both tool 172 and implant 170, which professional 26 inserts using tool 172.

Methods for Image-Guided Surgery Using Depth Sensing

Figure 4A:
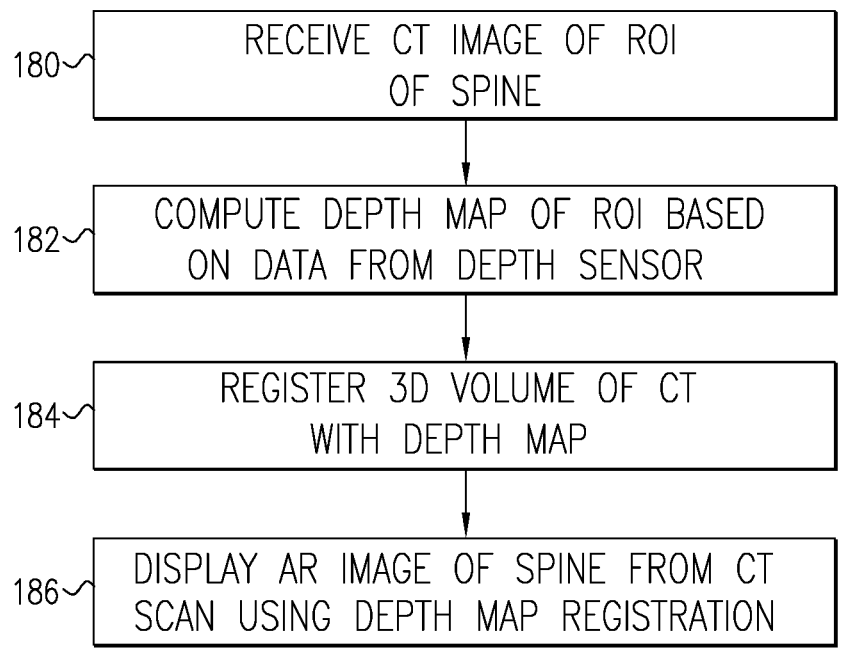
FIGS. 4A and 4B are flow charts that schematically illustrate methods for image-guided surgery, in accordance with embodiments of the disclosure.

FIG. 4A is a flow chart that schematically illustrates a method for image-guided surgery, in accordance with an embodiment of the disclosure. This method, as well as the methods presented in the figures that follow, is described here with reference to the elements of system 10 (as shown in FIGS. 1, 2A and 3A) for the sake of convenience and clarity. Alternatively, the principles of these methods may be applied, mutatis mutandis, in other sorts of augmented reality systems with suitable head-mounted units and depth sensing capabilities, including specifically the head-mounted units shown in FIG. 2B, as well as in the system shown in FIG. 8.

In some embodiments, the processing system 50 receives a 3D tomographic image, such as a CT image, of at least an ROI within the body, at an image input step 180. This image may be based on a scan or scans performed before and/or in the course of the surgical procedure. In some embodiments during the procedure, depth sensor 37 generates depth data with respect to the ROI, and processor 32 applies the depth data in computing a depth map of the ROI, at a depth mapping step 182. For example, the depth map may include the spine of patient 20, which may be exposed in a surgical procedure.

In some embodiments, the processor 32 registers the 3D volume of the tomographic image from the CT scan with the depth map, at a registration step 184. For this purpose, for example, processor 32 extracts 3D point clouds from both the tomographic image and the depth map and then computes a transformation to register one with the other. For instance, during surgery on the spine, the processor may compute the transformation by registering the spine in the depth map with the spine appearing in the tomographic image. Various methods for volume analysis may be used to perform the registration. In one embodiment, processor 32 computes triangular meshes based on the tomographic and depth data and then matches the features of the two meshes.

In some embodiments, the processor 32 applies the transformation computed at step 184 in presenting a part of the tomographic image on displays 30 of head-mounted unit 28 in registration with the ROI viewed through the displays, at a display step 186. In accordance with several embodiments, to display a tracked tool together with the display of the ROI in step 186, the depth sensor 37 (e.g., using cameras of the depth sensor 37) must be calibrated with the tracking system (e.g., tracking sensor 34). In some embodiments, the processor 32 may use the position of patient marker 38, as detected by camera 43 and/or tracking sensor 34, in improving the registration. For example, by identifying the position of patient marker 38 in the depth map, processor 32 may recognize where professional 26 is standing relative to the body of patient 20. In some embodiments, the processor will then rotate the AR image that is presented on head-mounted unit 28 automatically according to the position of the head-mounted unit relative to the patient marker.

In some embodiments, the processor 32 continues to receive and process depth data output by depth sensor 37 during the surgical procedure. In some embodiments, the processor identifies changes in anatomical structures in the body of patient 20 during the procedure, based on the corresponding changes in the depth map. For example, processor 32 can detect that a part of a bone has been cut or that an implant has been inserted or removed. On this basis, processor 32 can modify the AR image presented on the display of head-mounted unit 28 to reflect the identified change.

Figure 4B:
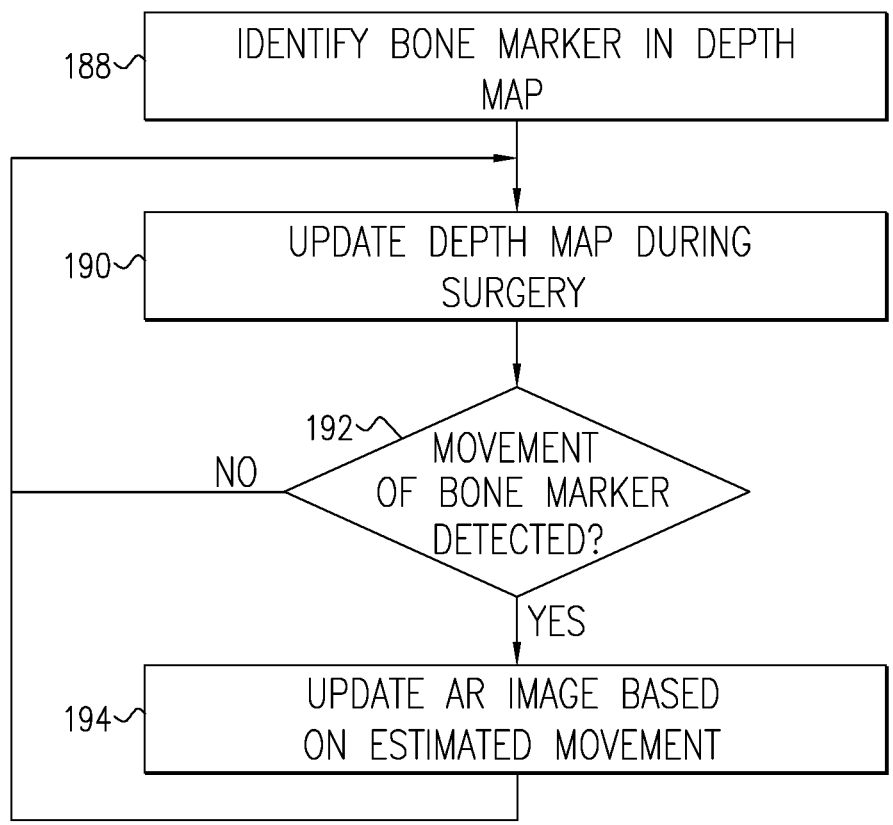

FIG. 4B is a flow chart that schematically illustrates a method for image-guided surgery, in accordance with another embodiment of the disclosure. This embodiment builds on the method of FIG. 4A and applies the method in detecting movement of the bone marker 60, and/or movement of a bone anchoring implement or device such as the bone clamp 58 relative to the bone to which it is attached, such as the patient's spine. Identification and measurement of such movement is important since it can affect the overall accuracy of system 10.

In some embodiments, the processor 32 identifies the location of bone marker 60 and/or the bone anchoring device in an initial depth map that is generated using depth sensor 37, at a bone marker and/or bone anchoring device identification step 188. In some embodiments, the depth map may be registered with the tomographic image of the patient's spine using the procedure of step 184 of FIG. 4A, as described above. In some embodiments, the processor 32 can thus use the depth data in accurately calculating the position of bone marker 60 and/or bone clamp 58 relative the patient's spine.

Subsequently, in the course of the surgery in some embodiments, the depth sensor 37 continues to capture depth data, and processor periodically updates the depth map, at a depth update step 190. In one embodiment, processor identifies bone marker 60 and/or bone clamp 58 in the updated depth map and checks whether the location of the clamp has shifted relative to the location of spine, as derived from the tomographic image, at a movement detection step 192. When the location of the clamp in the updated depth map has changed, processor 32 takes a corrective action. For example, the processor 32 may modify the image presented on display 30 to reflect this change, at an image update step 194. Additionally or alternatively, the processor 32 may issue a warning to the healthcare professional 26 that one of the markers has moved, such as the bone marker 60 or the patient marker 38, so that the professional can take corrective action if needed.

Figure 5:
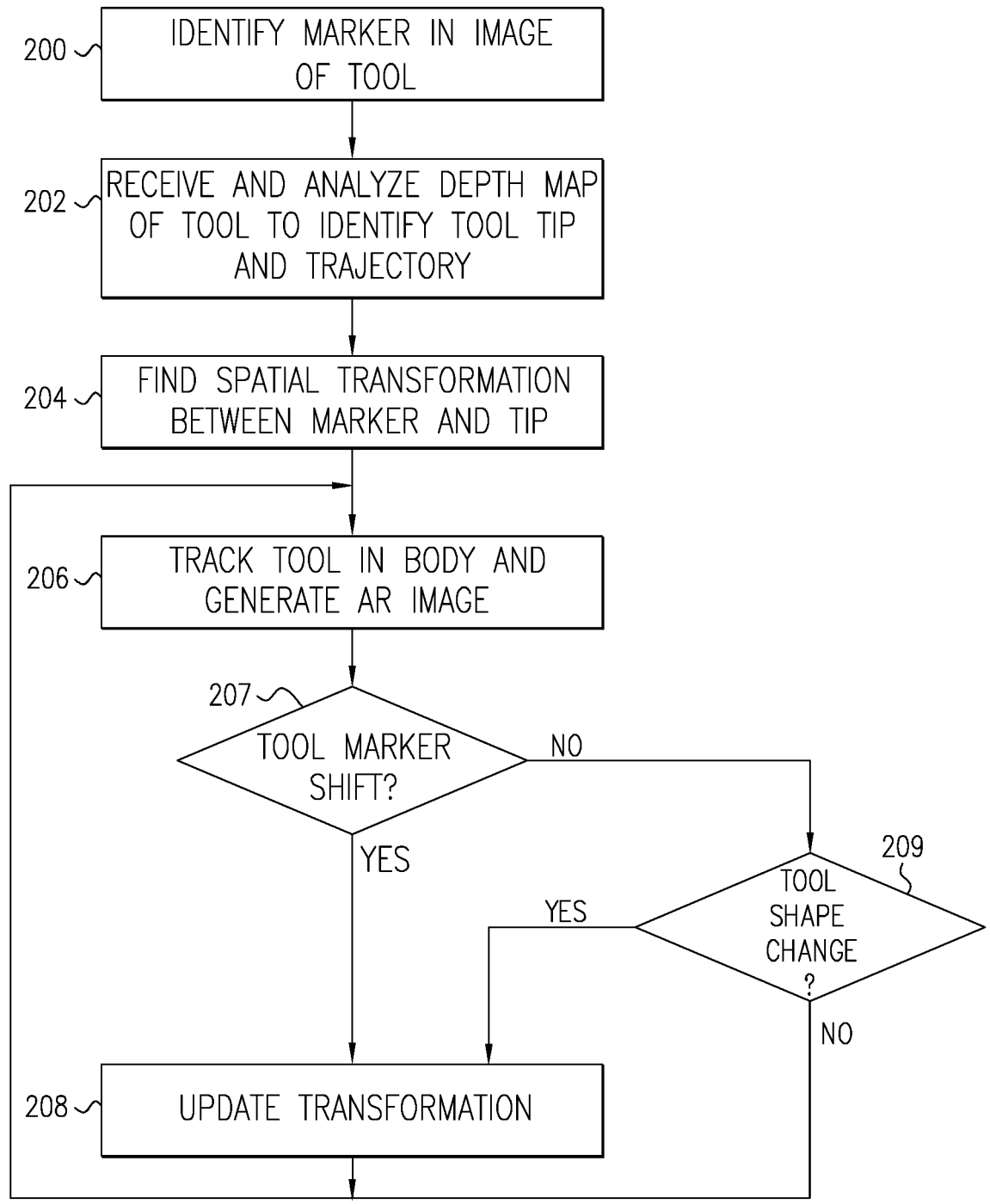
FIGS. 5, 6 and 7 are flow charts that schematically illustrate methods for image-guided surgery, in accordance with further embodiments of the disclosure.

FIG. 5 is a flow chart that schematically illustrates a method for image-guided surgery, in accordance with yet another embodiment of the disclosure. In some embodiments, the method uses both the 3D shape of the tool 22, which processor 32 derives from the depth data provided by depth sensor 37, and the position of the tool marker 40. The position of the tool marker 40 may be measured by tracking sensor 34, or it may alternatively be extracted from images captured by camera 43 of the depth sensor 37. In either case, in some embodiments, with all the elements used in finding the position of marker 40 and generating depth data with respect to tool 22 being fixed to the head-mounted unit 28 in a known spatial relation, the position of the marker will be consistently registered with the depth map.

In some embodiments, the method of FIG. 5 includes two calibration phases: The first phase includes performing initial calibration prior to the procedure. The second phase provides continuous calibration to update the initial calibration during the procedure. There may be two manners in which the initial calibration may be performed and then updated. In both manners, tool 22 and marker 40 (while the marker is mounted on the tool) are modeled by using depth sensing, for example to identify the trajectory and tip of the tool and the position of the marker with respect to the tool. In some embodiments, the processing system 50 then identifies the tool and marker and determines their relative locations. This function can be carried out using computer vision, for example using function of detection and segmentation, and optionally by applying machine learning techniques, including deep learning. Alternatively or additionally, tracking sensor 34 is used to identify the marker in the 3D model, in which case computer vision may be used only to identify the tool. In the continuous calibration update phase, either or both methods may be used, as well. Although the method shown in FIG. 5 and described below includes both calibration phases, aspects of the method may be applied only in the initial calibration without updating. Furthermore, although some steps in FIG. 5 and in the description below make use of tool marker 40, the method may alternatively be carried out, mutatis mutandis, using only depth sensing without reliance on a tool marker.

In some embodiments, the processor 32 identifies tool marker 40 in an image of tool 22, at a marker identification step 200. As noted earlier, the image may be provided either by tracking sensor 34 or by camera 43. In some embodiments, the processor 32 analyzes the image to derive the position of the tool marker.

In some embodiments, the processor 32 also processes depth data provided by depth sensor 37 in order to generate a depth map of tool 22, possibly along with other elements in the ROI, at a depth mapping step 202. In some embodiments, the processor 32 analyzes the shape of tool 22 in the depth map, for example using techniques of 3D image segmentation and/or machine learning that are known in the art. On this basis, for example, the processor 32 may identify shaft 164 (FIG. 3A) and is thus able to find the orientation of axis 166, corresponding to the "trajectory" of tool 22, and the location of distal end or tip 168. When the shaft of the tool is not straight, for example as in tool 172 (FIG. 3B), processor 32 may use the information provided by the depth map in modeling the tool and finding the location and orientation of the distal tip.

Based on the marker position found at step 200 and the depth map analysis of step 202, in some embodiments, the processor 32 computes a spatial transformation between the position of tool marker 40 and the location and orientation of shaft 164, at a transformation step 204. This transformation can be computed on the basis of the position of the marker and the depth data, without requiring prior knowledge of the shape of tool 22 or of the precise position of marker 40 relative to the other parts of the tool. Alternatively, a priori information regarding the position of the marker on the tool may be used to improve the accuracy of the transformation.

Using the tool marker 40 and/or updated depth data, the processor 32 tracks or may receive tracking information about the position of the tool 22 as professional 26 manipulates the tool with the shaft 164 inserted into the body (and thus not visible to depth sensor 37), at a tracking step 206. Using the tracked position and the spatial transformation computed at step 204, processor 32 generates an image of tool 22 on display 30, in registration with the ROI viewed through the display. The image specifically shows shaft 164, and particularly distal end 168, which when placed inside the patient's body may not be directly visible to professional 26.

As noted earlier, although tool marker 40 is shown in FIG. 3 as a part of handle 162, in other embodiments the tool marker may be fixed externally to the tool. In this case, the tool marker is liable to shift relative to the tool. Processor 32 analyzes the depth data provided by depth sensor 37 in order to calibrate the position of the tool marker relative to the tool. Thus, according to some embodiments, the processor may optionally update this analysis periodically at step 206 during the surgical procedure and checks the position to determine whether the tool marker has shifted relative to the tool, at a shift detection step 207. If so, processor 32 recalibrates the tool position to compensate for the shift, and based on the new calibration, updates the transformation that was computed previously (at step 204), at a transformation update step 208. The image presented on display 30 is modified accordingly.

It may also occur that the shape of tool 22 or tool 172 changes in the course of the surgical procedure. For example, the bending angle of shaft 174 may change, or the shaft may even break. Processor 32 analyzes the depth data provided by depth sensor 37 in order to determine whether the shape of the tool has changed, at a shape change detection step 209. If so, processor 32 recalibrates the tool shape to compensate for the change, and based on the new calibration, updates the transformation that was computed previously (at step 204), at transformation update step 208. The image of the tool on display 30 is updated, as well.

Figure 6:
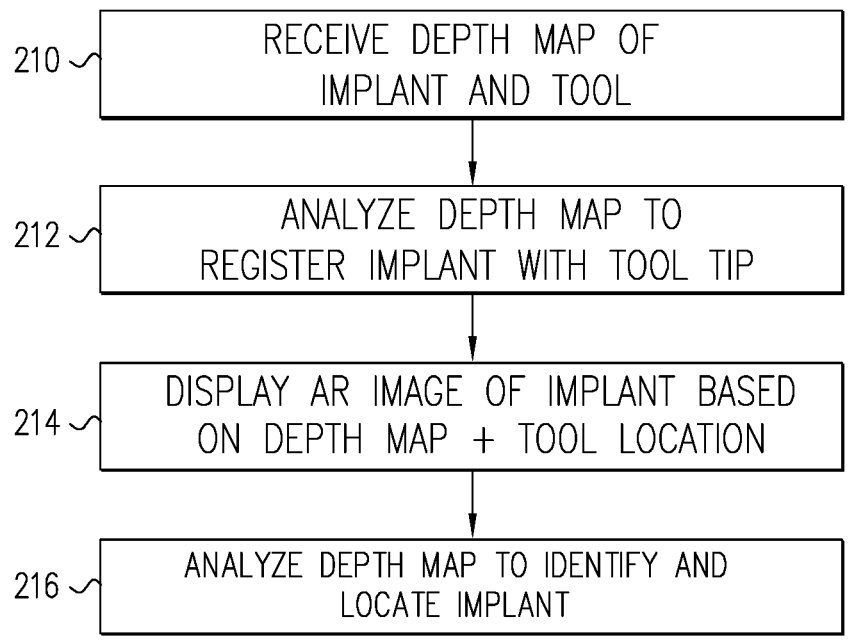

FIG. 6 is a flow chart that schematically illustrates a method for image-guided surgery, in accordance with a further embodiment of the disclosure. This embodiment extends the method of FIG. 5 to deal with the shape and position of implant 170, in addition to tool 22. Although FIG. 3 shows implant 170 as a screw (for example a pedicle screw), the present method is equally applicable to implants of other types, such as stents, cages, and interbody devices. The present method is advantageous in that it enables processor 32 to extract the shapes of implants without requiring prior knowledge of the implant characteristics, and to use the extracted shapes in presenting virtual images of the implants on display 30.

As an initial step, before inserting implant 170 into the body of patient 20, processor 32 generates (or accesses if depth maps were previously generated) depth maps of both implant 170 and tool 22, at a depth mapping step 210. For this purpose, for example, a user of system 10 may be prompted to operate depth sensor 37 to capture depth data with respect to implant 170 by itself and also with respect to tool 22 with implant 170 mounted on distal end 168. Processor 32 analyzes the depth data to identify the shape of implant 170. Based on this shape and on the depth map of implant 170 mounted on tool 22, processor 32 computes a spatial transformation between the position of the tip of tool 22 and the location and orientation of implant 170, at a registration step 212. A spatial transformation between the position of marker 40 and the location and orientation of implant 170 may be computed therefrom. Alternatively or additionally, a transformation between marker 40 and the tip of tool 22 may have been computed at an earlier phase, for example at a calibration phase as described above.

Following these steps, professional 26 uses tool 22 to insert implant 170 into the body of patient 20. Processor 32 tracks the position of marker 40 as professional 26 manipulates shaft 164 of tool 22 within the body. According to some aspects, such tracking information is accessed by processor 32. Using the tracked position, the spatial transformation computed at step 212, and the shape of the implant that was identified at step 210, processor 32 generates a virtual image on display 30 showing the implant within the body and/or its navigation, in registration with the ROI viewed through the display, at an image generation step 214.

After implant 170 has been inserted in place, processor 32 may continuing processing the depth data provided by depth sensor 37 in order to identify and locate the implant, at an implant tracking step 216. For example, processor 32 may identify the head of a screw in the depth map as a cue to the location and orientation of the screw. The display on head-mounted unit 28 can be modified to show the implant in the proper location. The information regarding the location and orientation of the implant can also be useful in planning subsequent stages of the procedure, such as insertion of rods between the screws.

Figure 7:
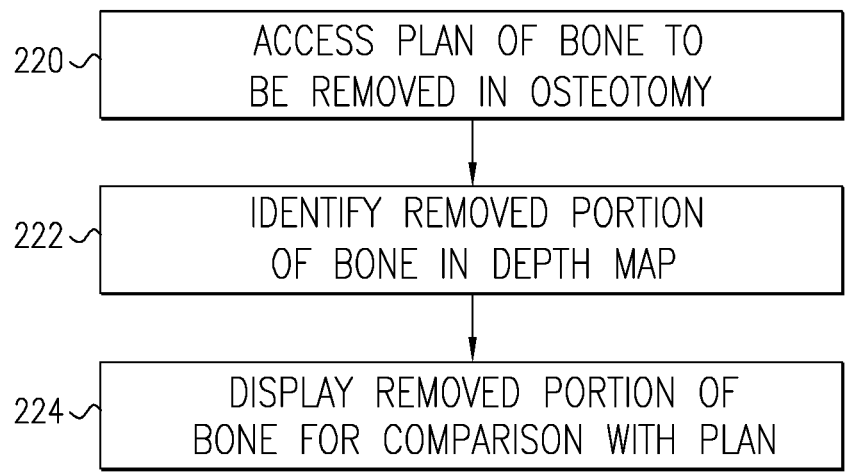

FIG. 7 is a flow chart that schematically illustrates a method for image-guided surgery, in accordance with an additional embodiment of the disclosure. This method is applicable particular in osteotomies, to assist in visualizing the portion of a bone that is removed in the procedure. In such a procedure, processing system 50 accesses a plan made by the surgeon to remove a certain volume of the bone in question, for example a part of one or more vertebrae, at a planning step 220. The present method can assist the surgeon in comparing the volume of the bone that has been cut out to the planned volume.

For this purpose, prior to cutting of the bone, the processor 32 processes depth data generated by depth sensor 37 so as to identify the 3D shape of the bone, for example by generating a point cloud. The 3D cutting plan can be overlaid on the patient's actual anatomy (without displaying patient image data), optionally in a semi- or partially-transparent manner. For example, the top plane of the plan can be overlaid on the patient in alignment with and oriented according to the patient anatomy. The plan may be used as a guide for cutting.

As the surgeon cuts the bone, the outline or indication of a plane of the bone to be removed according to plan changes according to the cutting tool tip location, for example based on depth of penetration. The plan outline or plane can be displayed from a point of view defined by the tool orientation, as determined by tracking the tool tracking. This mode is especially compatible with a "Tip View" mode, in which the patient spine model displayed on the near-eye display, generated based on CT data, changes according to the tool tip location and such that the upper surface of the model is the upper plane defined by the tool orientation and tip location. For example, the model may be cut up to a plane orthogonal to the tool trajectory or longitudinal orientation such that only a portion of the model is displayed.

It is also possible to display or indicate what was done already or the portion of the procedure already performed (e.g., what portion of the bone was already cut and what portion of the bone is left to be cut). The already-cut portion may be indicated on the plan, for example in a different color, or augmented on the image or on the actual patient anatomy or the plan may be updated to show only the remaining bone, and may also show when a portion of the bone was not cut according to plan. Tracking of the cutting may be performed based on tool tip tracking or by depth sensing.

To track cutting using depth sensing, a first depth image of the bone is captured prior to cutting. During the cutting, additional depth images are captured. The capturing may be performed on user request or automatically, continuously or at predefined time interval. Each depth image is compared to the previous one, and processor 32 identifies whether a bone portion was removed or not, i.e., whether cutting was performed. When a difference in the bone volume is identified, the portion of bone that was removed may be indicated on or compared to the plan and displayed to the user. The depth sensor and the tracking system may be calibrated for this purpose. Alternatively, or additionally, the depth maps may be registered with the CT model, for example using feature matching. The calibration and registration process may allow comparison between the different depth maps, the CT model, and the plan.

After the bone has been cut, in some embodiments, the processor 32 accesses and processes new depth data in order to identify the modified 3D shape of the bone. Based on the difference between the 3D shapes, processor 32 identifies the portion of the bone that was removed, at an excision identification step 222. In some embodiments, the processor 32 can then display an image showing the part of the bone that was removed in the surgical procedure, at a display step 224. The surgeon can compare this image to the plan in order to verify that the osteotomy was completed according to plan. In some embodiments, the processor 32 can display both images, i.e., of the removed bone volume and of the planned volume, simultaneously to facilitate comparison between the two. The images may be displayed adjacent to or overlaid on one another.

Alternatively, processor 32 may display to the surgeon only the removed portion of the bone, without comparison to a plan. The processor may thus demonstrate the removed volume and assist in confirming the procedure or in deciding whether a correction or a further operation is required, for example. Additionally or alternatively, in cases in which an implant is to be placed in the body in place of the removed portion of the bone, the surgeon and/or processor 32 may use the model of the removed bone portion to select a suitable implant or to determine whether a particular implant is suitable. On this basis, a suitable implant may be selected from a database, for example. When comparing the removed bone volume to a specific implant, size data may be provided with respect to the implant, or it may be generated using the depth sensing techniques described above.

In some embodiments, the processor 32 generates a model of the removed portion of the bone, which can be used as an input for an implant printing device (such as a 3D printer). The implant may thus be designed based on the model of the removed portion of bone.

In one embodiment, the image and/or model of the ROI that is presented on the AR display, such as the patient spine model, dynamically changes according to the cutting performed and based on the tracking of cutting that is described above. Thus, if a drill is used, for example, then holes may be formed in the model correspondingly, based on tool tracking, for example. The model may be updated in this manner during the procedure and during cutting. At the end of the procedure, the user may be presented with a model showing the entire bone portion removed.

Alternative Embodiment

Figure 8:
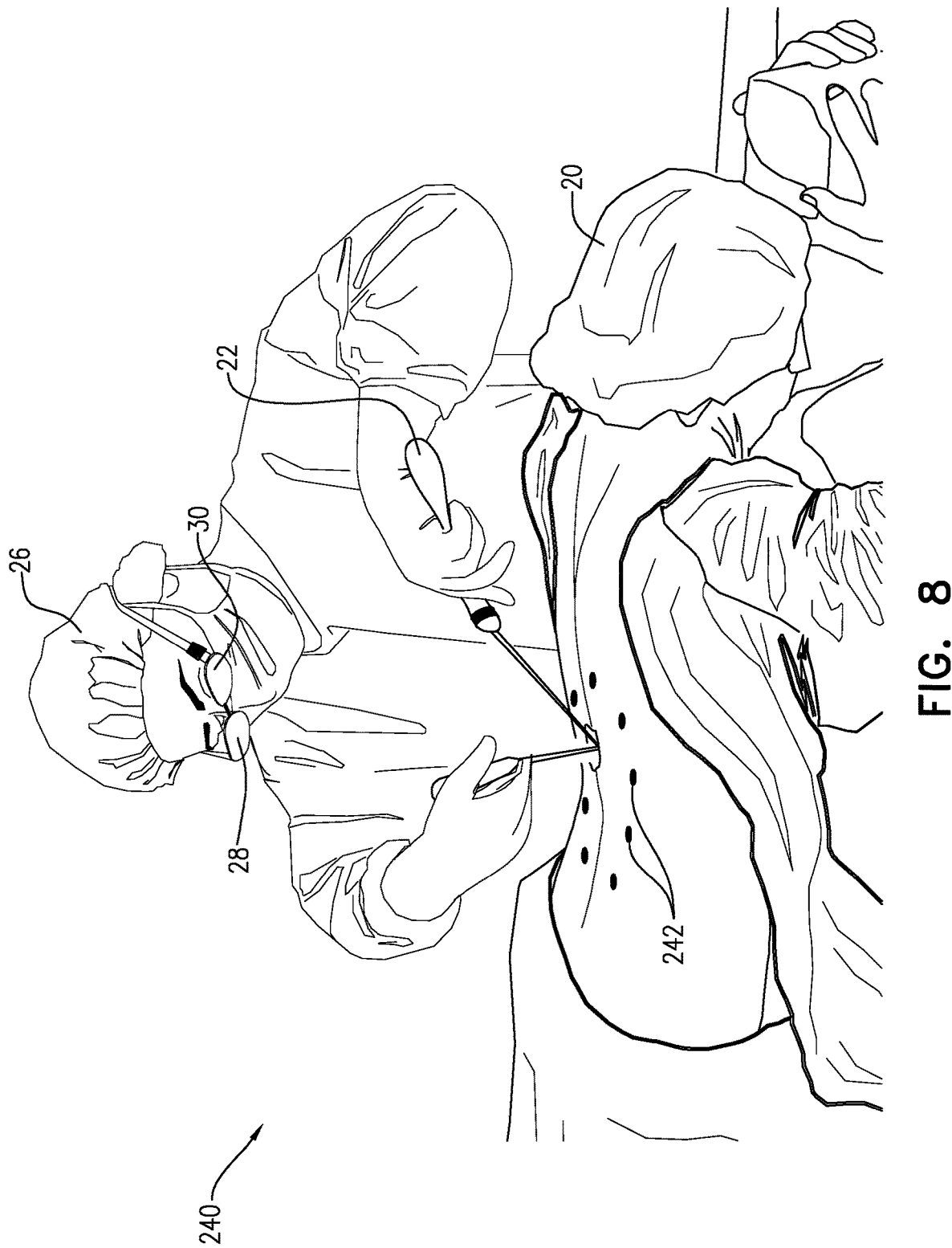
FIG. 8 is a schematic pictorial illustration showing a system for image-guided surgery, in accordance with an alternative embodiment of the disclosure.

FIG. 8 is a schematic pictorial illustration of a system 240 for image-guided surgery, in accordance with an alternative embodiment of the invention. System 240 is similar in design and operation to system 10 (FIG. 1), except that system 240 does not use the sorts of patient marker and clamp marker that were described above, with the accompanying tracking system. Rather, system 240 comprises an array of fiducial markers 242, which are fixed to the back of patient 20, for example using a suitable adhesive. Fiducial markers 242 comprises 3D elements, such as metal beads, which are both radiopaque and visible to cameras, such as camera 43 (FIG. 2A).

Prior to the surgical procedure, markers 242 are fixed to the back of patient 20, and a CT scan of the patient is performed, for example using CT scanner 41 (FIG. 1). Markers 242 will appear in the resulting CT images along with the patient's skeleton. During the surgery, depth sensor 37 on head-mounted unit 28 captures depth maps of the patient's back, including markers 242. Processor 32 analyzes the depth maps to find the 3D coordinates of markers 242. The processor then matches the locations of markers 242 in the CT image data with the 3D coordinates of the markers in the depth map, and thus derives the appropriate transformation to register the CT image data with the actual patient anatomy viewed by professional 26. Based on this registration, processor 32 presents parts of the CT images on displays 30, overlaid on the patient anatomy.

The other features and applications of depth mapping in image-guided surgery that are described above may likewise be applied, mutatis mutandis, in system 240.

Although the drawings and embodiments described above relate specifically to surgery on the spine, the principles of the present disclosure may similarly be applied in other sorts of surgical procedures, such as operations performed on the cranium and various joints, as well as dental surgery. It will thus be appreciated that the embodiments described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

Indeed, although the systems and processes have been disclosed in the context of certain embodiments and examples, it will be understood by those skilled in the art that the various embodiments of the systems and processes extend beyond the specifically disclosed embodiments to other alternative embodiments and/or uses of the systems and processes and obvious modifications and equivalents thereof. In addition, while several variations of the embodiments of the systems and processes have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosed systems and processes. Any methods disclosed herein need not be performed in the order recited. Thus, it is intended that the scope of the systems and processes herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and sub-combinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

The various features and processes described above may be used independently of one another or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

As used herein "generate" or "generating" may include specific algorithms for creating information based on or using other input information. Generating may include retrieving the input information such as from memory or as provided input parameters to the hardware performing the generating. Once obtained, the generating may include combining the input information. The combination may be performed through specific circuitry configured to provide an output indicating the result of the generating. The combination may be dynamically performed such as through dynamic selection of execution paths based on, for example, the input information, device operational characteristics (for example, hardware resources available, power level, power source, memory levels, network connectivity, bandwidth, and the like). Generating may also include storing the generated information in a memory location. The memory location may be identified as part of the request message that initiates the generating. In some implementations, the generating may return location information identifying where the generated information can be accessed. The location information may include a memory location, network locate, file system location, or the like.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by the processors 32, 45 described herein and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As it is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated. While the embodiments provide various features, examples, screen displays, user interface features, and analyses, it is recognized that other embodiments may be used.

What is claimed is:

1. A head-mounted system for image-guided surgery, comprising:
    a head-mounted unit, comprising a see-through augmented-reality display and a depth sensor, which is configured to generate depth data with respect to a body of a patient that is viewed through the display by a user wearing the head-mounted unit, the depth data including data for both a region of interest (ROI) within the body of the patient and an array of radiopaque fiducial markers fixed externally to the body of the patient; and
    a processor, which is configured to:
        receive a three-dimensional (3D) tomographic image of the body of the patient;
        compute a depth map based on the depth data generated by the depth sensor, the depth map including both the ROI within the body of the patient and the array of radiopaque fiducial markers fixed externally to the body of the patient;
        compute a transformation over the ROI so as to register the tomographic image with the depth map; and
        apply the transformation in presenting a part of the tomographic image on the display in registration with the ROI viewed through the display,
    wherein the ROI within the body of the patient that is included in the depth map includes a spine of the patient, which is exposed in a surgical procedure,
    wherein the processor is configured to compute the transformation by registering the spine in the depth map with the spine appearing in the tomographic image,
    wherein the tomographic image comprises a CT scan of the patient which was performed with the array of radiopaque fiducial markers fixed externally to the body of the patient,
    wherein the processor is configured to identify respective 3D coordinates of the fiducial markers in the depth map and to register the CT scan with the ROI viewed through the display by matching the fiducial markers in the CT to the respective 3D coordinates, and
    wherein the processor is configured to compute an updated depth map in a course of a surgery to enable detection of a change in the ROI within the body of the patient based on the updated depth map.

2. The system of claim 1, wherein the ROI comprises a bone of the body to which an anchoring device is coupled, and wherein the processor is further configured to:
    identify a location of the anchoring device in the depth map;
    detect a change in the location of the anchoring device in the updated depth map; and
    take a corrective action responsively to the change.

3. The system of claim 2, wherein the corrective action comprises modifying a presentation on the display responsively to the change in the location of the anchoring device.

4. The system of claim 1, wherein the processor is configured to:
    process the updated depth map so as to identify a change in an anatomical structure in the body of the patient during the surgery; and
    modify the image presented on the display responsively to the identified change.

5. The system of claim 1, wherein the processor is configured to:
    process the updated depth map so as to identify an implant inserted into the body of the patient during the surgery; and
    modify the image presented on the display responsively to the identified implant.

6. The system of claim 1, wherein the 3D tomographic image is a computed tomographic image.

7. The system of claim 1, wherein the depth sensor comprises a pattern projector and a camera configured for structured-light depth mapping.

8. The system of claim 7, wherein the pattern projector comprises a laser dot pattern projector configured to apply structured light comprising dots arranged in a pattern.

9. The system of claim 8, wherein the pattern is a pseudorandom pattern of dots.

10. The system of claim 9, wherein the depth map is calculated based on a local disparity of images of the pattern captured by the camera relative to an undistorted reference pattern, together with a known offset between the pattern projector and the camera.

11. The system of claim 1, wherein the depth sensor comprises a pair of cameras configured for stereoscopic depth mapping.

12. The system of claim 1, wherein the depth sensor comprises a beam projector and one or more detectors configured for time-of-flight measurement.

13. The system of claim 1, wherein the head-mounted unit comprises a head strap.

14. The system of claim 1, wherein the head-mounted unit comprises a visor.

15. The system of claim 1, wherein the processor is further configured to:
 process the depth map to identify a 3D shape of a vertebrae bone prior to a cutting of the vertebrae bone;
 process the updated depth map to identify a modified 3D shape of the vertebrae bone after the cutting of the vertebrae bone;
 based on a difference between the 3D shape and the modified 3D shape, identify a portion of the vertebrae bone that was removed; and
 present an image on the display showing the identified portion of the vertebrae bone that was removed.

16. A head-mounted system for image-guided surgery comprising:
 a see-through augmented-reality display disposed so as to be viewable by a user over a body of a patient;
 a depth sensor configured to generate depth data with respect to the body of the patient, the depth data including data for both a region of interest (ROI) within the body of the patient and one or more markers positioned external to the body of the patient; and
 a processor and a memory for storing instructions that, when executed by the processor cause the system to:
  receive a three-dimensional (3D) tomographic image of the body of the patient;
  determine a depth map based at least in part on the depth data, the depth map including both the ROI within the body of the patient and the one or more markers positioned external to the body of the patient;
  determine a transformation over the ROI so as to register the 3D tomographic image with the depth map;
  display at least a part of the 3D tomographic image on the see-through augmented-reality display in registration with the ROI based at least in part on the transformation; and
  determine an updated depth map in a course of a surgery to enable detection of a change in the ROI within the body of the patient based on the updated depth map.

17. The system of claim 16, wherein:
 the 3D tomographic image is a computed tomographic image;
 the depth sensor comprises a pattern projector and a camera configured for structured-light depth mapping; and
 the pattern projector comprises a laser dot pattern projector configured to apply structured light comprising dots arranged in a pattern.

18. The system of claim 17, wherein the pattern is a pseudorandom pattern of dots.

19. The system of claim 18, wherein the depth map is calculated based on a local disparity of images of the pattern captured by the camera relative to an undistorted reference pattern, together with a known offset between the pattern projector and the camera.

20. The system of claim 16, further comprising a head-mounted unit comprising the see-through augmented-reality display.

* * * * *